United States Patent
Li et al.

(10) Patent No.: US 9,055,869 B2
(45) Date of Patent: Jun. 16, 2015

(54) METHODS AND SYSTEMS FOR PHOTOACOUSTIC SIGNAL PROCESSING

(75) Inventors: Youzhi Li, Longmont, CO (US); Bo Chen, Louisville, CO (US)

(73) Assignee: COVIDIEN LP, Mansfield, MA (US)

( * ) Notice: Subject to any disclaimer, the term of this patent is extended or adjusted under 35 U.S.C. 154(b) by 894 days.

(21) Appl. No.: 13/284,568

(22) Filed: Oct. 28, 2011

(65) Prior Publication Data
US 2013/0109949 A1    May 2, 2013

(51) Int. Cl.
| | |
|---|---|
| *A61B 5/1455* | (2006.01) |
| *A61B 8/02* | (2006.01) |
| *A61B 5/00* | (2006.01) |
| *G01N 21/17* | (2006.01) |
| *G01N 21/31* | (2006.01) |
| *G01N 21/47* | (2006.01) |
| *A61B 5/021* | (2006.01) |

(52) U.S. Cl.
CPC ... *A61B 8/02* (2013.01); *A61B 5/72* (2013.01); *A61B 5/14551* (2013.01); *G01N 21/1702* (2013.01); *G01N 21/314* (2013.01); *G01N 21/4738* (2013.01); *A61B 5/0095* (2013.01); *A61B 5/021* (2013.01)

(58) Field of Classification Search
CPC ............. A61B 5/1455; A61B 5/14551; A61B 5/0095; A61B 5/72
USPC .................. 600/310, 322, 323, 324, 326, 328
See application file for complete search history.

(56) References Cited

U.S. PATENT DOCUMENTS

| | | |
|---|---|---|
| 4,385,634 A | 5/1983 | Bowen |
| 5,348,002 A | 9/1994 | Caro |
| 5,657,754 A | 8/1997 | Rosencwaig |
| 5,840,023 A | 11/1998 | Oraevsky et al. |
| 5,941,821 A | 8/1999 | Chou |
| 6,049,728 A | 4/2000 | Chou |
| 6,104,942 A | 8/2000 | Kruger |

(Continued)

FOREIGN PATENT DOCUMENTS

| | | |
|---|---|---|
| EP | 0282234 | 9/1988 |
| JP | 2007259918 | 10/2007 |
| WO | WO2009/055705 | * 4/2009 |

OTHER PUBLICATIONS

International Search Report and Written Opinion of the International Searching Authority for application No. PCT/US 2012/062328, mailed on Feb. 7, 2013.

(Continued)

*Primary Examiner* — Eric Winakur
(74) *Attorney, Agent, or Firm* — Fletcher Yoder PC

(57) ABSTRACT

A physiological monitoring system may perform an optical measurement of a subject to assist a photoacoustic analysis of the subject. For example, an oblique-incidence diffuse reflectance measurement, photon density wave measurement, or other optical measurement may be used to determine one or more optical properties of a subject. Accordingly, the one or more optical properties may be used to determine an optical fluence at a region of the subject. In some arrangements, a physiological monitoring system may include an oximeter, and may use a calculated blood oxygen saturation value to assist a photoacoustic analysis. Photoacoustic analysis may include determining one or more physiological parameters based on a detected acoustic pressure response of a subject to a photonic signal via the photoacoustic effect.

20 Claims, 7 Drawing Sheets

(56) References Cited

U.S. PATENT DOCUMENTS

| | | | |
|---|---|---|---|
| 6,309,352 | B1 | 10/2001 | Oraevsky et al. |
| 6,403,944 | B1 | 6/2002 | MacKenzie et al. |
| 6,405,069 | B1 | 6/2002 | Oraevsky et al. |
| 6,466,806 | B1 | 10/2002 | Geva et al. |
| 6,484,044 | B1 | 11/2002 | Lilienfeld-Toal |
| 6,498,942 | B1 | 12/2002 | Esenaliev et al. |
| 6,751,490 | B2 | 6/2004 | Esenaliev et al. |
| 6,839,496 | B1 | 1/2005 | Mills et al. |
| 6,846,288 | B2 | 1/2005 | Nagar et al. |
| 7,322,972 | B2 | 1/2008 | Viator et al. |
| 7,430,445 | B2 | 9/2008 | Esenaliev et al. |
| 7,515,948 | B1 | 4/2009 | Balberg et al. |
| 7,729,734 | B2 | 6/2010 | Mandelis et al. |
| 2004/0039379 | A1 | 2/2004 | Viator et al. |
| 2006/0184042 | A1 | 8/2006 | Wang et al. |
| 2006/0272418 | A1 | 12/2006 | Maris et al. |
| 2007/0197886 | A1 | 8/2007 | Naganuma et al. |
| 2008/0255433 | A1 | 10/2008 | Prough et al. |
| 2010/0285518 | A1 | 11/2010 | Viator et al. |
| 2010/0292547 | A1 | 11/2010 | Mandelis et al. |
| 2011/0071373 | A1 | 3/2011 | Li et al. |
| 2011/0201914 | A1 | 8/2011 | Wang et al. |
| 2011/0275890 | A1 | 11/2011 | Wang et al. |
| 2012/0029829 | A1 | 2/2012 | Li et al. |

OTHER PUBLICATIONS

Brecht, Hans-Peter, "Noninvasive Optoacoustic Monitoring of Blood Oxygenation in Large Blood Vessels," Thesis, The University of Texas Medical Branch, Dec. 2007, pp. i-xviii; 1-131.

Esenaliev, Rinat O., et al., "Continuous, Noninvasive Monitoring of Total Hemoglobin Concentration by an Optoacoustic Technique," Applied Optics, vol. 43, No. 17, 2007, pp. 3401-3407.

Fan, Ying, et al., "Laser Photothermoacoustic Heterodyned Lock-in Depth Profilometry in Turbid Tissue Phantoms," Phys. Rev. E, vol. 72, 2005, pp. 051908.1-051908.11.

Guo, Zijian, et al., "On the Speckle-free Nature of Photoacoustic Tomography," Med. Phys., vol. 37, No. 9, 2009, pp. 4084-4088.

Guo, Zijian, et al., "Calibration-free Absolute Quantification of Optical Absorption Coefficients Using Acoustic Spectra in 3D Photoacoustic Microscopy of Biological Tissue," Optics Letters, vol. 35, 2010, pp. 2067-2069.

Hu, Song, et al., "Noninvasive Label-free Imaging of Microhemodynamics by Optical-resolution Photoacoustic Microscopy," Optics Express, vol. 17, No. 9, 2009, pp. 7688-7693.

Larina, Irina V., et al., "Real-Time Optoacoustic Monitoring of Temperature in Tissues," J. Phys. D: Appl. Phys., vol. 38, 2005, pp. 2633-2639.

Laufer, Jan, et al., "In Vitro Measurements of Absolute Blood Oxygen Saturation Using Pulsed Near-Infrared Photoacoustic Spectroscopy: Accuracy and Resolution," Phys. Med. Biol., vol. 50, 2005, pp. 4409-4428.

Petrova, Irina Y., et al., "Clinical Tests of Highly Portable, 2-lb, Laser Diode-based, Noninvasive, Optoacoustic Hemoglobin Monitor," Proc. of SPIE, vol. 7177, 2009, pp. 717705•1-717705•6.

Pramanik, Manojit, et al., "Thermoacoustic and Photoacoustic Sensing of Temperature," Journal of Biomedical Optics, vol. 14, No. 5, 2009, pp. 054024•1-054024•7.

Ranasinghesagara, Janaka C., et al., "Combined Photoacoustic and Oblique-incidence Diffuse Reflectance System for Quantitative Photoacoustic Imaging in Turbid Media," Journal of Biomedical Optics, vol. 15, No. 4, 2010, pp. 046016•1-046016•5.

Telenkov, Sergey A., et al., "Photothermoacoustic Imaging of Biological Tissues: Maximum Depth Characterization Comparison of Time and Frequency-domain Measurements," Journal of Biomedical Optics, vol. 14, No. 4, 2009, 044025•1-044025•12.

\* cited by examiner

METHODS AND SYSTEMS FOR PHOTOACOUSTIC SIGNAL PROCESSING

The present disclosure relates to physiological signal processing, and more particularly relates to determining physiological information from a photoacoustic signal.

SUMMARY

A physiological monitoring system may be configured to determine a physiological parameter using photoacoustic analysis and optical analysis of a subject. The system may perform an optically-based measurement to aid the photoacoustic analysis of a photoacoustic signal. In some embodiments, an optical fluence at a location within the subject may be estimated to aid in determining the physiological parameter from the photoacoustic signal.

In some embodiments, an oblique-incidence diffuse reflectance (OIR) measurement may be used to aid in determining a physiological parameter. A photodetector may detect an attenuated (e.g., reflected) photonic signal arising from attenuation by the subject of a photonic signal, which may be provided by a light source of the physiological monitoring system. Additionally, an acoustic detector may detect acoustic pressure signals arising from absorption of a frequency modulated, continuous wave photonic signal, which may be provided by a light source of the physiological monitoring system.

In some embodiments, a photon density wave (PDW) measurement may be used to aid in determining a physiological parameter. A photodetector may detect an attenuated (e.g., reflected, transmitted) photonic signal arising from attenuation by the subject of a photonic signal, which may be provided by a light source of the physiological monitoring system. Additionally, an acoustic detector may detect acoustic pressure signals arising from absorption of a photonic signal, which may be provided by a light source of the physiological monitoring system.

The detected attenuated photonic signal (e.g., from an OIR or PDW measurement) may be used to determine one or more optical properties of the subject such as, for example, an absorption coefficient, scattering coefficient, and/or and attenuation coefficient. The optical property may be used to estimate an optical fluence at a region of interest within the subject, using a correlation, lookup table or model. The estimated optical fluence may be used to adjust the photoacoustic signal, and allow a more accurate determination of the one or more physiological parameters. Physiological parameters may include blood oxygen saturation (e.g., $SpO_2$, $SvO_2$), hemoglobin concentration (e.g., tHb), pulse rate, any other suitable physiological parameters, or any combination thereof.

In some embodiments, an oximeter may be used to determine a blood oxygen saturation, which may be used to aid a photoacoustic analysis. The blood oxygen saturation, as determined by the oximeter, may be used to adjust a total hemoglobin concentration value determined from a photoacoustic signal. In some embodiments, the blood oxygen saturation determined by the oximeter may be used to aid in determining a venous blood oxygen saturation. The use of an oximeter to augment a photoacoustic measurement may be especially useful for subjects experiencing hypoxia, for example.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
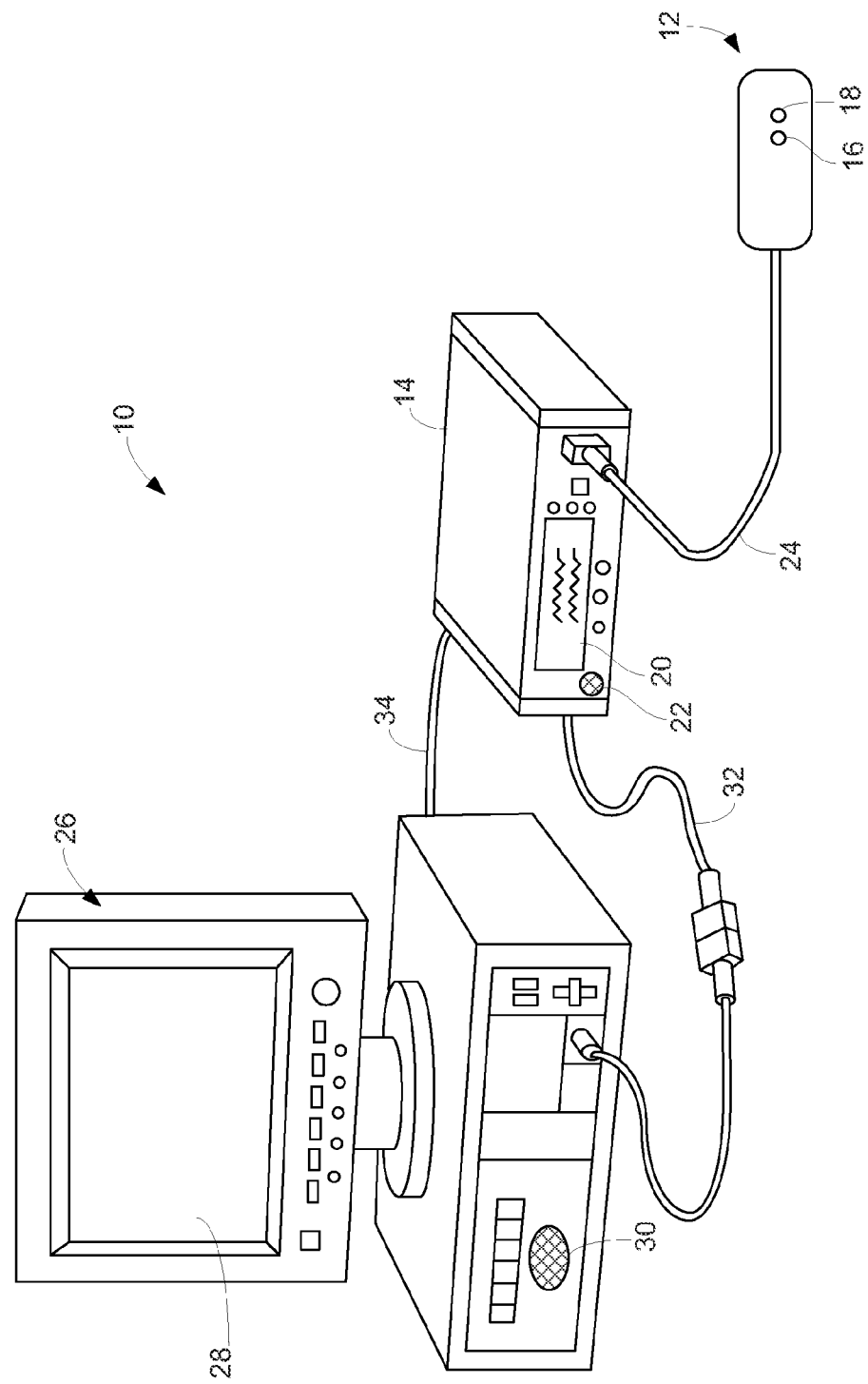
FIG. 1 shows an illustrative physiological monitoring system, in accordance with some embodiments of the present disclosure.

Photoacoustics (or "optoacoustics") or the photoacoustic effect (or "optoacoustic effect") refers to the phenomenon in which one or more wavelengths of light are presented to and absorbed by one or more constituents of an object, thereby causing an increase in kinetic energy of the one or more constituents, which causes an associated pressure response within the object. Particular modulations or pulsing of the incident light, along with measurements of the corresponding pressure response in, for example, tissue of the subject, may be used for medical imaging, physiological parameter determination, or both. For example, the concentration of a constituent, such as hemoglobin (e.g., oxygenated, deoxygenated and/or total hemoglobin) may be determined using photoacoustic analysis.

A photoacoustic system may include a photoacoustic sensor that is placed at a site on a subject, typically the wrist, palm, neck, forehead, temple, or anywhere an artery or vessel is accessible noninvasively. In some embodiments, the photoacoustic techniques described herein are used to monitor large blood vessels, such as a major artery or vein which may be near the heart (e.g., the carotid or radial arteries or the jugular vein). The photoacoustic system may use a light source, and any suitable light guides (e.g., fiber optics), to pass light through the subject's tissue, or a combination of tissue thereof (e.g., organs), and an acoustic detector to sense the pressure response of the tissue induced by the light absorption by a blood vessel. Tissue may include muscle, fat, blood, blood vessels, and/or any other suitable tissue types. In some embodiments, the light source may be a laser or laser diode, operated in pulsed or continuous wave (CW) mode. In some embodiments, the acoustic detector may be an ultrasound detector, which may be suitable to detect pressure fluctuations arising from the constituent's absorption of the incident light of the light source.

In some embodiments, the light from the light source may be focused, shaped, or otherwise spatially modulated to illuminate a particular region of interest. In some arrangements, photoacoustic monitoring may allow relatively higher spatial resolution than line of sight optical techniques (e.g., path integrated absorption measurements). The enhanced spatial resolution of the photoacoustic technique may allow for imaging, scalar field mapping, and other spatially resolved results, in 1, 2, or 3 spatial dimensions. The acoustic response to the photonic excitation may radiate from the illuminated region of interest, and accordingly may be detected at multiple positions.

The photoacoustic system may measure the pressure response that is received at the acoustic sensor as a function of time. The photoacoustic system may also include sensors at multiple locations. A signal representing pressure versus time or a mathematical manipulation of this signal (e.g., a scaled version thereof, etc.) may be referred to as the photoacoustic (PA) signal. The PA signal may be used to calculate any of a number of physiological parameters, including an amount of a blood constituent (e.g., oxy-hemoglobin), at a particular spatial location. In some embodiments, PA signals from multiple spatial locations may be used to construct an image (e.g., imaging blood vessels) or a scalar field (e.g., a hemoglobin concentration field).

In some applications, the light passed through the tissue is selected to be of one or more wavelengths that are absorbed by the constituent in an amount representative of the amount of the constituent present in the tissue. The absorption of light passed through the tissue varies in accordance with the amount of the constituent in the tissue. For example, Red and/or infrared (IR) wavelengths may be used because highly oxygenated blood will absorb relatively less Red light and more IR light than blood with a lower oxygen saturation.

Any suitable light source may be used, and characteristics of the light provided by the light source may be controlled in any suitable manner. In some embodiments, a pulsed light source may be used to provide relatively short-duration pulses (e.g., nanosecond pulses) of light to the region of interest. Accordingly, the use of a pulse light source may result in a relatively broadband acoustic response (e.g., depending on the pulse duration). The use of a pulsed light source will be referred to herein as the "Time Domain Photoacoustic" (TD-PA) technique. A convenient starting point for analyzing a TD-PA signal is given by Eq. 1:

$$p(z) = \Gamma \mu_a \phi(z) \tag{1}$$

under conditions where the irradiation time is small compared to the characteristic thermal diffusion time determined by the properties of the specific tissue type. Referring to Eq. 1, p(z) is the PA signal (indicative of the maximum induced pressure rise) at spatial location z indicative of acoustic pressure, $\Gamma$ is the dimensionless Grüneisen parameter of the tissue, $\mu_a$ is the effective absorption coefficient of the tissue (or constituent thereof) to the incident light, and $\phi(z)$ is the optical fluence at spatial location z. The Grüneisen parameter is a dimensionless description of thermoelastic effects, and may be illustratively formulated by Eq. 2:

$$\Gamma = \frac{\beta c_a^2}{C_p} \tag{2}$$

where $c_a^2$ is the speed of sound in the tissue, $\beta$ is the isobaric volume thermal expansion coefficient, and $C_p$ is the specific heat at constant pressure. In some circumstances, the optical fluence, at spatial location z (within the subject's tissue) of interest may be dependent upon the light source, the location itself (e.g., the depth), and optical properties (e.g., scattering coefficient, absorption coefficient, or other properties) along the optical path. For example, Eq. 3 provides an illustrative expression for the attenuated optical fluence at a depth z:

$$\phi(z) = \phi_0 e^{-\mu_{eff} z} \tag{3}$$

where $\phi_0$ is the optical fluence from the light source incident at the tissue surface, z is the path length (i.e., the depth into the tissue in this example), and $\mu_{eff}$ is an effective attenuation coefficient of the tissue along the path length in the tissue in this example.

In some embodiments, a more detailed expression or model may be used rather than the illustrative expression of Eq. 3. In some embodiments, the actual pressure encountered by an acoustic detector may be proportional to Eq. 1, as the focal distance and solid angle (e.g., face area) of the detector may affect the actual measured PA signal. In some embodiments, an ultrasound detector positioned relatively farther away from the region of interest, will encounter a relatively smaller acoustic pressure. For example, the acoustic pressure received at a circular area $A_d$ positioned at a distance R from the illuminated region of interest may be given by Eq. 4:

$$p_d = p(z) f(r_s, R, A_d) \tag{4}$$

where $r_s$ is the radius of the illuminated region of interest (and typically $r_s < R$), and p(z) is given by Eq. 1. In some embodiments, the detected acoustic pressure amplitude may decrease as the distance R increases (e.g., for a spherical acoustic wave).

In some embodiments, a modulated CW light source may be used to provide a photonic excitation of a tissue constituent to cause a photoacoustic response in the tissue. The CW light source may be intensity modulated at one or more characteristic frequencies. The use of a CW light source, intensity modulated at one or more frequencies, will be referred to herein as the "Frequency Domain Photoacoustic" (FD-PA) technique. Although the FD-PA technique may include using frequency domain analysis, the technique may use time domain analysis, wavelet domain analysis, or any other suitable analysis, or any combination thereof. Accordingly, the term "frequency domain" as used in "FD-PA" refers to the frequency modulation of the photonic signal, and not to the type of analysis used to process the photoacoustic response.

Under some conditions, the acoustic pressure p(R,t) at detector position R at time t, may be shown illustratively by Eq. 5:

$$p(R, t) \sim \frac{p_0(r_0, \omega)}{R} e^{-i\omega(t-\tau)} \tag{5}$$

where $r_0$ is the position of the illuminated region of interest, $\omega$ is the angular frequency of the acoustic wave (caused by modulation of the photonic signal at frequency $\omega$), R is the distance between the illuminated region of interest and the detector, and $\tau$ is the travel time delay of the wave equal to $R/c_a$, where $c_a$ is the speed of sound in the tissue. The FD-PA spectrum $p_0(r_0,\omega)$ of acoustic waves is shown illustratively by Eq. 6:

$$p_0(r_0, \omega) = \frac{\Gamma \mu_a \phi(r_0)}{2(\mu_a c_a - i\omega)} \tag{6}$$

where $\mu_a c_a$ represents a characteristic frequency (and corresponding time scale) of the tissue.

In some embodiments, a FD-PA system may temporally vary the characteristic modulation frequency of the CW light source, and accordingly the characteristic frequency of the associated acoustic response. For example, the FD-PA system may use linear frequency modulation (LFM), either increasing or decreasing with time, which is sometimes referred to as "chirp" signal modulation. Shown in Eq. 7 is an illustrative expression for a sinusoidal chirp signal r(t):

$$r(t) = \sin\left(t\left(\omega_0 + \frac{b}{2}t\right)\right) \tag{7}$$

where $\omega_0$ is a starting angular frequency, and b is the angular frequency scan rate. Any suitable range of frequencies (and corresponding angular frequencies) may be used for modulation such as, for example, 1-5 MHz, 200-800 kHz, or other suitable range, in accordance with the present disclosure. In some embodiments, signals having a characteristic frequency that changes as a nonlinear function of time may be used. Any suitable technique, or combination of techniques thereof, may be used to analyze a FD-PA signal. Two such exemplary techniques, a correlation technique and a heterodyne mixing technique, will be discussed below as illustrative examples.

In some embodiments, the correlation technique may be used to determine the travel time delay of the FD-PA signal. In some embodiments, a matched filtering technique may be used to process a PA signal. As shown in Eq. 8:

$$B_s(t-\tau) = \frac{1}{2\pi}\int_{-\infty}^{\infty} H(\omega)S(\omega)e^{i\omega t}\, d\omega \tag{8}$$

Fourier transforms (and inverse transforms) are used to calculate the filter output $B_s(t-T)$, in which $H(\omega)$ is the filter frequency response, $S(\omega)$ is the Fourier transform of the PA signal s(t), and T is the phase difference between the filter and signal. In some circumstances, the filter output of expression of Eq. 8 may be equivalent to an autocorrelation function. Shown in Eq. 9:

$$S(\omega) = \frac{1}{2\pi}\int_{-\infty}^{\infty} s(t)e^{-i\omega t}\, dt \tag{9}$$

is an expression for computing the Fourier transform $S(\omega)$ of the PA signal s(t). Shown in Eq. 10:

$$H(\omega) = S^*(\omega)e^{-i\omega\tau} \tag{10}$$

is an expression for computing the filter frequency response $H(\omega)$ based on the Fourier transform of the PA signal s(t). It can be observed that the filter frequency response of Eq. 10 requires the frequency character of the PA signal be known beforehand to determine the frequency response of the filter. In some embodiments, as shown by Eq. 11:

$$B(t) = \int_{-\infty}^{\infty} r(t')s(t+t')\, dt' \tag{11}$$

the known modulation signal r(t) may be used for generating a cross-correlation with the PA signal. The cross-correlation output B(t) of Eq. 11 is expected to exhibit a peak at a time t equal to the acoustic signal travel time $\tau$. Assuming that the temperature response and resulting acoustic response follow the illumination modulation (e.g., are coherent), Eq. 11 may allow calculation of the time delay, depth information, or both.

In some embodiments, the heterodyne mixing technique may be used to determine the travel time delay of the FD-PA signal. The FD-PA signal, as described above, may have similar frequency character as the modulation signal (e.g., coherence), albeit shifted in time due to the travel time of the acoustic signal. For example, a chirp modulation signal, such as r(t) of Eq. 7, may be used to modulate a CW light source. Heterodyne mixing uses the trigonometric identity of the following Eq. 12:

$$\sin(A)\sin(B) = \frac{1}{2}[\cos(A-B) - \cos(A+B)] \tag{12}$$

which shows that two signals may be combined by multiplication to give periodic signals at two distinct frequencies (i.e., the sum and the difference of the original frequencies). If the result is passed through a low-pass filter to remove the higher frequency term (i.e., the sum), the resulting filtered, frequency shifted signal may be analyzed. For example, Eq. 13 shows a heterodyne signal L(t):

$$L(t) = \langle r(t)s(t)\rangle \tag{13}$$
$$\cong \left\langle Kr(t)r\left(t - \frac{R}{c_a}\right)\right\rangle$$
$$= \frac{1}{2}K\cos\left(\frac{R}{c_a}bt + \theta\right)$$

calculated by low-pass filtering (shown by angle brackets) the product of modulation signal r(t) and PA signal s(t). If the PA signal is assumed to be equivalent to the modulation signal, with a time lag $R/c_a$ due to travel time of the acoustic wave and amplitude scaling K, then a convenient approximation of Eq. 13 may be made, giving the rightmost term of Eq. 13. Analysis of the rightmost expression of Eq. 13 may provide depth information, travel time, or both. For example, a fast Fourier transform (FFT) may be performed on the heterodyne signal, and the frequency associated with the highest peak may be considered equivalent to time lag $Rb/c_a$. Assuming that the frequency scan rate b and the speed of sound $c_a$ are known, the depth R may be estimated.

FIG. 1 is a perspective view of an embodiment of a physiological monitoring system 10. System 10 may include sensor unit 12 and monitor 14. In some embodiments, sensor unit 12 may be part of a photoacoustic monitor or imaging system. Sensor unit 12 may include a light source 16 for emitting light at one or more wavelengths into a subject's tissue. A detector 18 may also be provided in sensor unit 12 for detecting the acoustic (e.g., ultrasound) response that travels through the subject's tissue. Any suitable physical configuration of light source 16 and detector 18 may be used. In an embodiment, sensor unit 12 may include multiple light sources and/or acoustic detectors, which may be spaced apart. System 10 may also include one or more additional sensor units (not shown) that may take the form of any of the embodiments described herein with reference to sensor unit 12. An additional sensor unit may be the same type of sensor unit as sensor unit 12, or a different sensor unit type than sensor unit 12 (e.g., a photoplethysmograph sensor). Multiple sensor units may be capable of being positioned at two different locations on a subject's body.

In some embodiments, system 10 may include two or more sensors forming a sensor array in lieu of either or both of the sensor units. In some embodiments, a sensor array may include multiple light sources, detectors, or both. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, sensor unit 12 may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data relating to light emission and acoustic detection received from one or more sensor units such as sensor unit 12. For example, monitor 14 may be configured to determine pulse rate, blood pressure, blood oxygen saturation (e.g., arterial, venous, or both), hemoglobin concentration (e.g., oxygenated, deoxygenated, and/or total), any other suitable physiological parameters, or any combination thereof. In some embodiments, calculations may be performed on the sensor units or an intermediate device and the result of the calculations may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a subject's physiological parameters are not within a predefined normal range. In some embodiments, the system 10 includes a stand-alone monitor in communication with the monitor 14 via a cable or a wireless network link.

In some embodiments, sensor unit 12 may be communicatively coupled to monitor 14 via a cable 24. Cable 24 may include electronic conductors (e.g., wires for transmitting electronic signals from detector 18), optical fibers (e.g., multi-mode or single-mode fibers for transmitting emitted light from light source 16), any other suitable components, any suitable insulation or sheathing, or any combination thereof. In some embodiments, a wireless transmission device (not shown) or the like may be used instead of or in addition to cable 24. Monitor 14 may include a sensor interface configured to receive physiological signals from sensor unit 12, provide signals and power to sensor unit 12, or otherwise communicate with sensor unit 12. The sensor interface may include any suitable hardware, software, or both, which may be allow communication between monitor 14 and sensor unit 12.

In the illustrated embodiment, system 10 includes a multi-parameter physiological monitor 26. The monitor 26 may include a cathode ray tube display, a flat panel display (as shown) such as a liquid crystal display (LCD) or a plasma display, or may include any other type of monitor now known or later developed. Multi-parameter physiological monitor 26 may be configured to calculate physiological parameters and to provide a display 28 for information from monitor 14 and from other medical monitoring devices or systems (not shown). For example, multi-parameter physiological monitor 26 may be configured to display an estimate of a subject's blood oxygen saturation and hemoglobin concentration generated by monitor 14. Multi-parameter physiological monitor 26 may include a speaker 30.

Monitor 14 may be communicatively coupled to multi-parameter physiological monitor 26 via a cable 32 or 34 that is coupled to a sensor input port or a digital communications port, respectively and/or may communicate wirelessly (not shown). In addition, monitor 14 and/or multi-parameter physiological monitor 26 may be coupled to a network to enable the sharing of information with servers or other workstations (not shown). Monitor 14 may be powered by a battery (not shown) or by a conventional power source such as a wall outlet.

Figure 2:
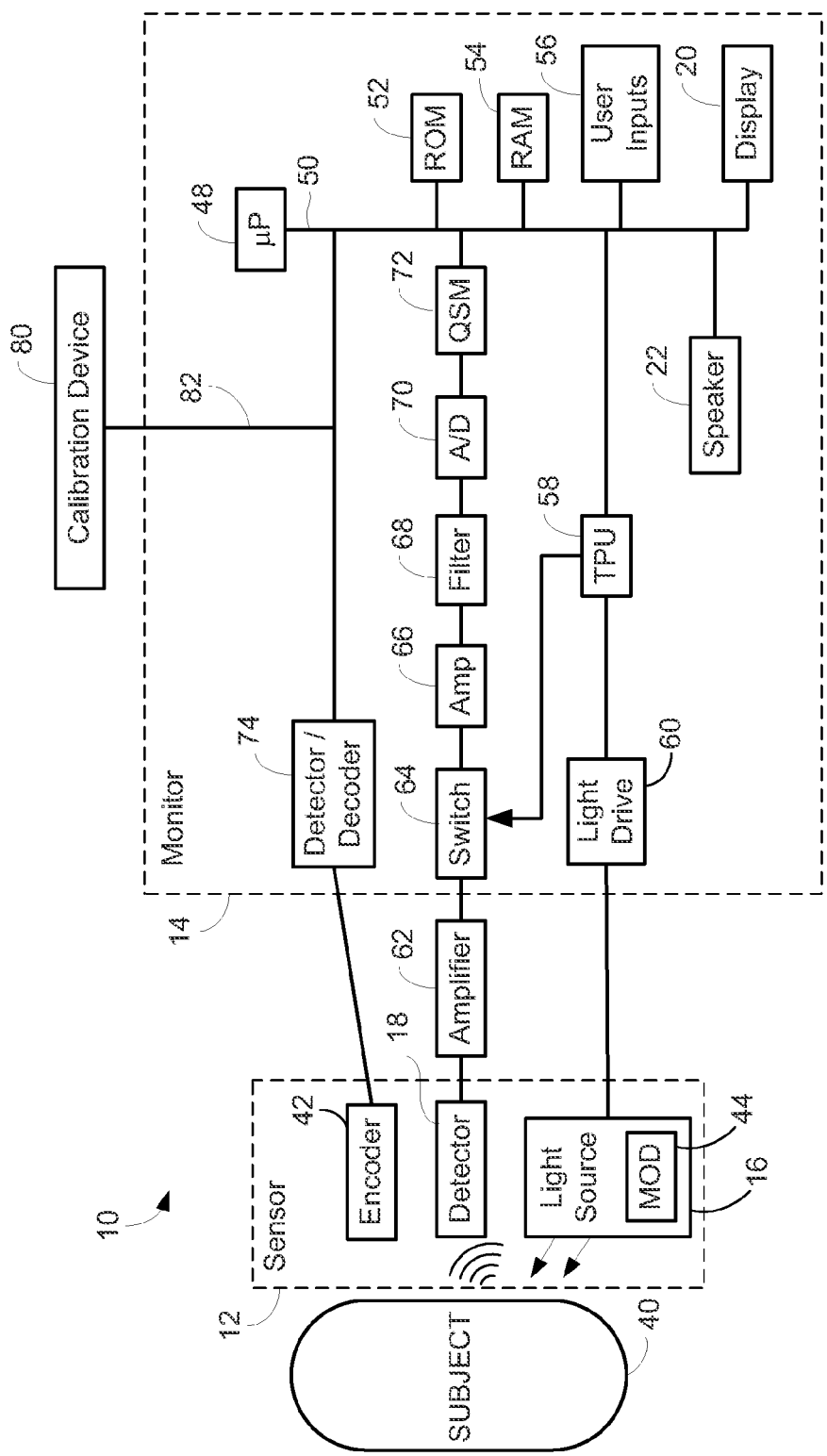
FIG. 2 is a block diagram of the illustrative physiological monitoring system of FIG. 1 coupled to a subject, in accordance with some embodiments of the present disclosure.

FIG. 2 is a block diagram of a physiological monitoring system, such as physiological monitoring system 10 of FIG. 1, which may be coupled to a subject 40 in accordance with an embodiment. Certain illustrative components of sensor unit 12 and monitor 14 are illustrated in FIG. 2.

Sensor unit 12 may include light source 16, detector 18, and encoder 42. In some embodiments, light source 16 may be configured to emit one or more wavelengths of light (e.g., visible, infrared) into a subject's tissue 40. Hence, light source 16 may provide Red light, IR light, any other suitable light, or any combination thereof, that may be used to calculate the subject's physiological parameters. In some embodiments, the Red wavelength may be between about 600 nm and about 700 nm, and the IR wavelength may be between about 800 nm and about 1000 nm. In embodiments where a sensor array is used in place of a single sensor, each sensor may be configured to provide light of a single wavelength. For example, a first sensor may emit only a Red light while a second may emit only an IR light. In a further example, the wavelengths of light used may be selected based on the specific location of the sensor.

It will be understood that, as used herein, the term "light" may refer to energy produced by electromagnetic radiation sources. Light may be of any suitable wavelength and intensity, and modulations thereof, in any suitable shape and direction. Detector 18 may be chosen to be specifically sensitive to the acoustic response of the subject's tissue arising from use of light source 16. It will also be understood that, as used herein, the "acoustic response" shall refer to pressure and changes thereof caused by a thermal response (e.g., expansion and contraction) of tissue to light absorption by the tissue or constituent thereof.

In some embodiments, detector 18 may be configured to detect the acoustic response of tissue to the photonic excitation caused by the light source. In some embodiments, detector 18 may be a piezoelectric transducer which may detect force and pressure and output an electrical signal via the piezoelectric effect. In some embodiments, detector 18 may be a Faby-Pérot interferometer, or etalon. For example, a thin film (e.g., composed of a polymer) may be irradiated with reference light, which may be internally reflected by the film. Pressure fluctuations may modulate the film thickness, thus causing changes in the reference light reflection which may be measured and correlated with the acoustic pressure. In some embodiments, detector 18 may be configured or otherwise tuned to detect acoustic response in a particular frequency range. Detector 18 may convert the acoustic pressure signal into an electrical signal (e.g., using a piezoelectric material, photodetector of a Faby-Pérot interferometer, or other suitable device). After converting the received acoustic pressure signal to an electrical signal, detector 18 may send the signal to monitor 14, where physiological parameters may be calculated based on the photoacoustic activity within the subject's tissue 40.

In some embodiments, encoder 42 may contain information about sensor unit 12, such as what type of sensor it is (e.g., where the sensor is intended to be placed on a subject), the wavelength(s) of light emitted by light source 16, the intensity of light emitted by light source 16 (e.g., output wattage or Joules), the mode of light source 16 (e.g., pulsed versus CW), any other suitable information, or any combination thereof. This information may be used by monitor 14 to select appropriate algorithms, lookup tables and/or calibration coefficients stored in monitor 14 for calculating the subject's physiological parameters.

Encoder 42 may contain information specific to subject 40, such as, for example, the subject's age, weight, and diagnosis. This information about a subject's characteristics may allow monitor 14 to determine, for example, subject-specific threshold ranges in which the subject's physiological parameter measurements should fall and to enable or disable additional physiological parameter algorithms. Encoder 42 may, for instance, be a coded resistor that stores values corresponding to the type of sensor unit 12 or the type of each sensor in the sensor array, the wavelengths of light emitted by light source 16 on each sensor of the sensor array, and/or the subject's characteristics. In some embodiments, encoder 42 may include a memory on which one or more of the following information may be stored for communication to monitor 14: the type of the sensor unit 12; the wavelengths of light emitted by light source 16; the particular acoustic range that each sensor in the sensor array is monitoring; a signal threshold for each sensor in the sensor array; any other suitable information; or any combination thereof.

In some embodiments, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium that can be used to store the desired information and that can be accessed by components of the system.

In the embodiment shown, a time processing unit (TPU) 58 may provide timing control signals to light drive circuitry 60, which may control the activation of light source 16. For example, TPU 58 may control pulse timing (e.g., pulse duration and inter-pulse interval) for TD-PA monitoring system. TPU 58 may also control the gating-in of signals from detector 18 through amplifier 62 and switching circuit 64. The received signal from detector 18 may be passed through amplifier 66, low pass filter 68, and analog-to-digital converter 70. The digital data may then be stored in a queued serial module (QSM) 72 (or buffer) for later downloading to RAM 54 as QSM 72 is filled. In some embodiments, there may be multiple separate parallel paths having components equivalent to amplifier 66, filter 68, and/or A/D converter 70 for multiple light wavelengths or spectra received. Any suitable combination of components (e.g., microprocessor 48, RAM 54, analog to digital converter 70, any other suitable component shown or not shown in FIG. 2) coupled by bus 50 or otherwise coupled (e.g., via an external bus), may be referred to as "processing equipment."

In the embodiment shown, light source 16 may include modulator 44, in order to, for example, perform FD-PA analysis. Modulator 44 may be configured to provide intensity modulation, spatial modulation, any other suitable optical signal modulations, or any combination thereof. For example, light source 16 may be a CW light source, and modulator 44 may provide intensity modulation of the CW light source such as using a linear sweep modulation. In some embodiments, modulator 44 may be included in light drive 60, or other suitable components of physiological monitoring system 10, or any combination thereof.

In some embodiments, microprocessor 48 may determine the subject's physiological parameters, such as $SpO_2$, $SvO_2$, oxy-hemoglobin concentration, deoxy-hemoglobin concentration, total hemoglobin concentration (tHb), and/or pulse rate, using various algorithms and/or lookup tables based on the value of the received signals and/or data corresponding to the acoustic response received by detector 18. Signals corresponding to information about subject 40, and particularly about the acoustic signals emanating from a subject's tissue over time, may be transmitted from encoder 42 to decoder 74. These signals may include, for example, encoded information relating to subject characteristics. Decoder 74 may translate these signals to enable the microprocessor to determine the thresholds based at least in part on algorithms or lookup tables stored in ROM 52. In some embodiments, user inputs 56 may be used enter information, select one or more options, provide a response, input settings, any other suitable inputting function, or any combination thereof. User inputs 56 may be used to enter information about the subject, such as age, weight, height, diagnosis, medications, treatments, and so forth. In some embodiments, display 20 may exhibit a list of values, which may generally apply to the subject, such as, for example, age ranges or medication families, which the user may select using user inputs 56.

Calibration device 80, which may be powered by monitor 14 via a communicative coupling 82, a battery, or by a conventional power source such as a wall outlet, may include any suitable signal calibration device. Calibration device 80 may be communicatively coupled to monitor 14 via communicative coupling 82, and/or may communicate wirelessly (not shown). In some embodiments, calibration device 80 is completely integrated within monitor 14. In some embodiments, calibration device 80 may include a manual input device (not shown) used by an operator to manually input reference signal measurements obtained from some other source (e.g., an external invasive or non-invasive physiological measurement system).

The acoustic signal attenuated by the tissue of subject 40 can be degraded by noise, among other sources. Movement of the subject may also introduce noise and affect the signal. For example, the contact between the detector and the skin, or the light source and the skin, can be temporarily disrupted when movement causes either to move away from the skin. Another source of noise is electromagnetic coupling from other electronic instruments.

Noise (e.g., from subject movement) can degrade a sensor signal relied upon by a care provider, without the care provider's awareness. This is especially true if the monitoring of the subject is remote, the motion is too small to be observed, or the care provider is watching the instrument or other parts of the subject, and not the sensor site. Processing sensor signals may involve operations that reduce the amount of noise present in the signals, control the amount of noise present in the signal, or otherwise identify noise components in order to prevent them from affecting measurements of physiological parameters derived from the sensor signals.

Figure 3:
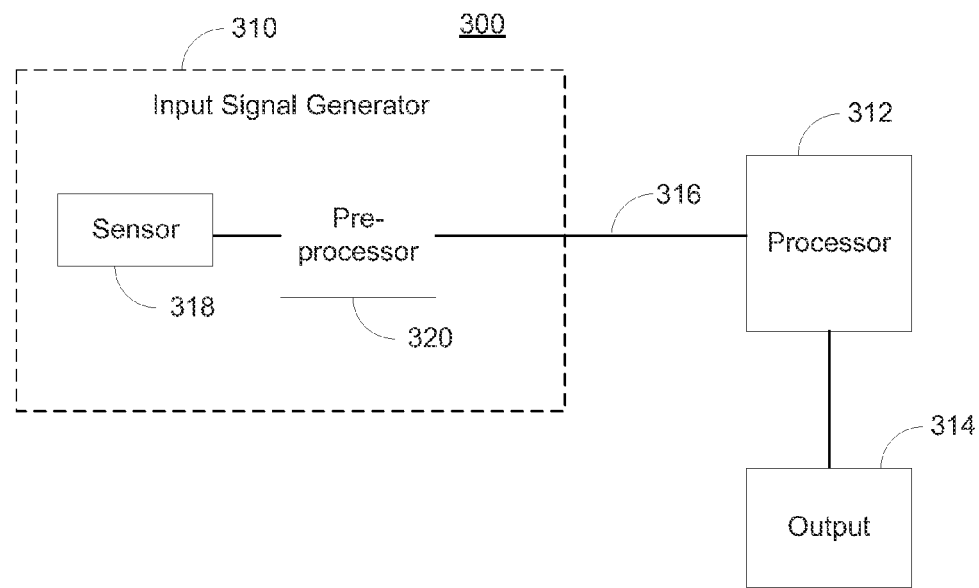
FIG. 3 is a block diagram of an illustrative signal processing system in accordance with some embodiments of the present disclosure.

FIG. 3 is an illustrative signal processing system 300 in accordance with an embodiment that may implement the signal processing techniques described herein. In some embodiments, signal processing system 300 may be included in a physiological monitoring system (e.g., physiological monitoring system 10 of FIGS. 1-2). In the illustrated embodiment, input signal generator 310 generates an input signal 316. As illustrated, input signal generator 310 may include pre-processor 320 coupled to sensor 318, which may provide input signal 316. In some embodiments, pre-processor 320 may be a photoacoustic module and input signal 316 may be a photoacoustic signal. In an embodiment, pre-processor 320 may be any suitable signal processing device and input signal 316 may include one or more photoacoustic signals and one or more other physiological signals, such as a photoplethysmograph signal. It will be understood that input signal generator 310 may include any suitable signal source, signal generating data, signal generating equipment, or any combination thereof to produce signal 316. Signal 316 may be a single signal, or may be multiple signals transmitted over a single pathway or multiple pathways.

Pre-processor 320 may apply one or more signal processing operations to the signal generated by sensor 318. For example, pre-processor 320 may apply a pre-determined set of processing operations to the signal provided by sensor 318 to produce input signal 316 that can be appropriately interpreted by processor 312, such as performing A/D conversion. In some embodiments, A/D conversion may be performed by processor 312. Pre-processor 320 may also perform any of the following operations on the signal provided by sensor 318: reshaping the signal for transmission, multiplexing the signal, modulating the signal onto carrier signals, compressing the signal, encoding the signal, and filtering the signal.

In some embodiments, signal 316 may be coupled to processor 312. Processor 312 may be any suitable software, firmware, hardware, or combination thereof for processing signal 316. For example, processor 312 may include one or more hardware processors (e.g., integrated circuits), one or more software modules, and computer-readable media such as memory, firmware, or any combination thereof. Processor 312 may, for example, be a computer or may be one or more chips (i.e., integrated circuits). Processor 312 may, for example, include an assembly of analog electronic components. Processor 312 may calculate physiological information. For example, processor 312 may perform time domain calculations, spectral domain calculations, time-spectral transformations (e.g., fast Fourier transforms, inverse fast Fourier transforms), any other suitable calculations, or any combination thereof. Processor 312 may perform any suitable signal processing of signal 316 to filter signal 316, such as any suitable band-pass filtering, adaptive filtering, closed-loop filtering, any other suitable filtering, and/or any combination thereof. Processor 312 may also receive input signals from additional sources (not shown). For example, processor 312 may receive an input signal containing information about treatments provided to the subject. Additional input signals may be used by processor 312 in any of the calculations or operations it performs in accordance with processing system 300.

In some embodiments, all or some of pre-processor 320, processor 312, or both, may be referred to collectively as processing equipment. For example, processing equipment may be configured to amplify, filter, sample and digitize signal 316 (e.g., using an analog to digital converter), and calculate physiological information from the digitized signal.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. In some embodiments, processor 312 may store physiological measurements or previously received data from signal 316 in a memory device for later retrieval. In some embodiments, processor 312 may store calculated values, such as pulse rate, blood pressure, blood oxygen saturation (e.g., arterial, venous, or both), hemoglobin concentration (e.g., oxygenated, deoxygenated, and/or total), or any other suitable calculated values, in a memory device for later retrieval.

Processor 312 may be coupled to output 314. Output 314 may be any suitable output device such as one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as part of sensor unit 12 (FIGS. 1 and 2) and monitor 14 (FIGS. 1 and 2) and processor 312 may be implemented as part of monitor 14 (FIGS. 1 and 2). In some embodiments, portions of system 300 may be configured to be portable. For example, all or part of system 300 may be embedded in a small, compact object carried with or attached to the subject (e.g., a watch, other piece of jewelry, or a smart phone). In some embodiments, a wireless transceiver (not shown) may also be included in system 300 to enable wireless communication with other components of system 10 (FIGS. 1 and 2). As such, system 10

(FIGS. 1 and 2) may be part of a fully portable and continuous physiological monitoring solution. In some embodiments, a wireless transceiver (not shown) may also be included in system 300 to enable wireless communication with other components of system 10. For example, pre-processor 320 may output signal 316 (e.g., which may be a pre-processed photoacoustic signal) over BLUETOOTH, IEEE 802.11, WiFi, WiMax, cable, satellite, Infrared, any other suitable transmission scheme, or any combination thereof. In some embodiments, a wireless transmission scheme may be used between any communicating components of system 300.

The PA signal obtained by system 10 or 300 is dependent on the optical fluence at the illuminated region of interest, as shown in Eq. 1, for example. While, the output of the light source may be modulated, measured, regulated, or otherwise controlled, the resulting light output may be attenuated along its pathlength prior to illumination of the region of interest. Accurately estimating the optical fluence at the region of interest may improve the accuracy of the resulting PA calculations.

In some embodiments, the optical fluence at the region of interest may be estimated by independently measuring, modeling, or both, the radiative properties of the tissue. For example, in some embodiments, an oblique-incidence diffuse reflectance (OIR) system may be used to estimate optical properties of an attenuating media (e.g., a subject's tissue). In a further example, in some embodiments, a pulse photon density wave (PDW) analysis may be used to determine the optical properties of an attenuating media (e.g., a subject's tissue). Techniques such as OIR, PDW, or other suitable optical characterization techniques, may be used with TD-PA analysis, FD-PA analysis, or both, to determine physiological information.

Figure 4:
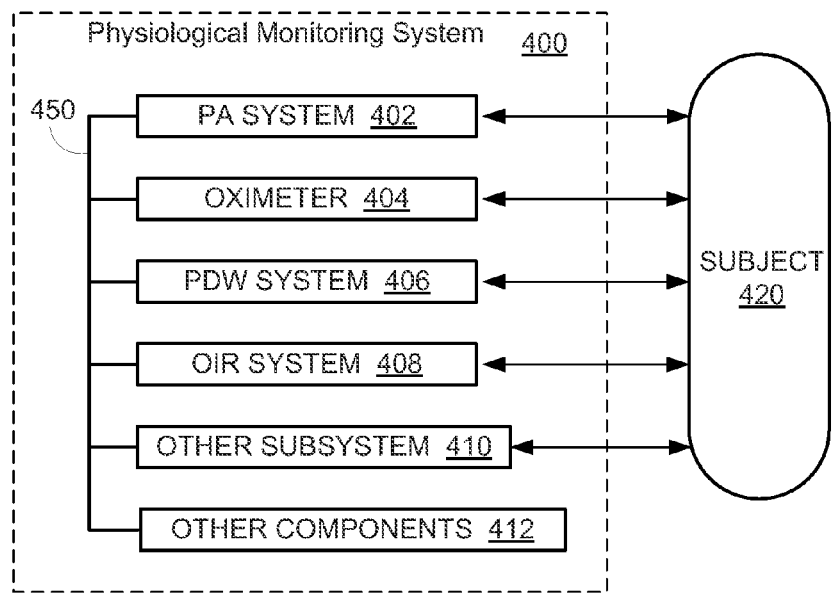
FIG. 4 is a block diagram of an illustrative physiological monitoring system, including several illustrative subsystems, in accordance with some embodiments of the present disclosure.

FIG. 4 is a block diagram of an illustrative physiological monitoring system 400, including several illustrative subsystems, in accordance with some embodiments of the present disclosure. Physiological monitoring system 400 may include photoacoustic system 402, oximeter 404, photon density wave system 406, oblique-incidence diffuse reflectance system 408, any other suitable subsystem 410, any other suitable components 412, or any combination thereof. Other components 410 may include any components of system 10, any components of system 300, any other suitable components, or any combination thereof. In some embodiments, one or more subsystems may be modules, configured to perform particular measurements, and also configured to communicate with one another. Accordingly, each subsystem may be a module, coupled to at least one other module via a communications bus 450, which may be a wired bus, wireless bus, any other suitable bus, or any combination thereof. For example, oximeter 404 may include RED and IR LEDs, activated by time-division multiplexing using a TPU, a photodetector configured to detect attenuated RED and IR light, and suitable processing equipment configured to determine an SpO$_2$ value of the subject. Oximeter 404 may communicate the determined SpO$_2$ value to any other suitable system coupled to communications bus 450, for example. In some embodiments, multiple sensor types may be configured to communicatively couple to a single processor. For example, system 10 or system 300 may be configured to accept multiple sensors such as PA sensors, PPG sensors, OIR sensors, PDW sensors, any other suitable sensors, or any combination thereof. Processor 312 may be configured to perform PA analysis, PPG analysis, OIR analysis, PDW analysis, any other suitable analysis, or any combination thereof. In some embodiments, each subsystem may include a suitable pre-processor and processor (e.g., pre-processor 320 and processor 312). In some embodiments, the one or more subsystems may each be separate systems, which may, but need not, communicate with one another. For example, PDW system 406 may be a standalone system, and may output optical information on a display. An operator may input the optical information into photoacoustic system 402, and suitable analysis may be performed by photoacoustic system 402. In some embodiments, system 400 may include any of the capabilities, components, or both, of system 10 and system 300. Any suitable configuration may be used to perform the disclosed analyses.

Figure 5:
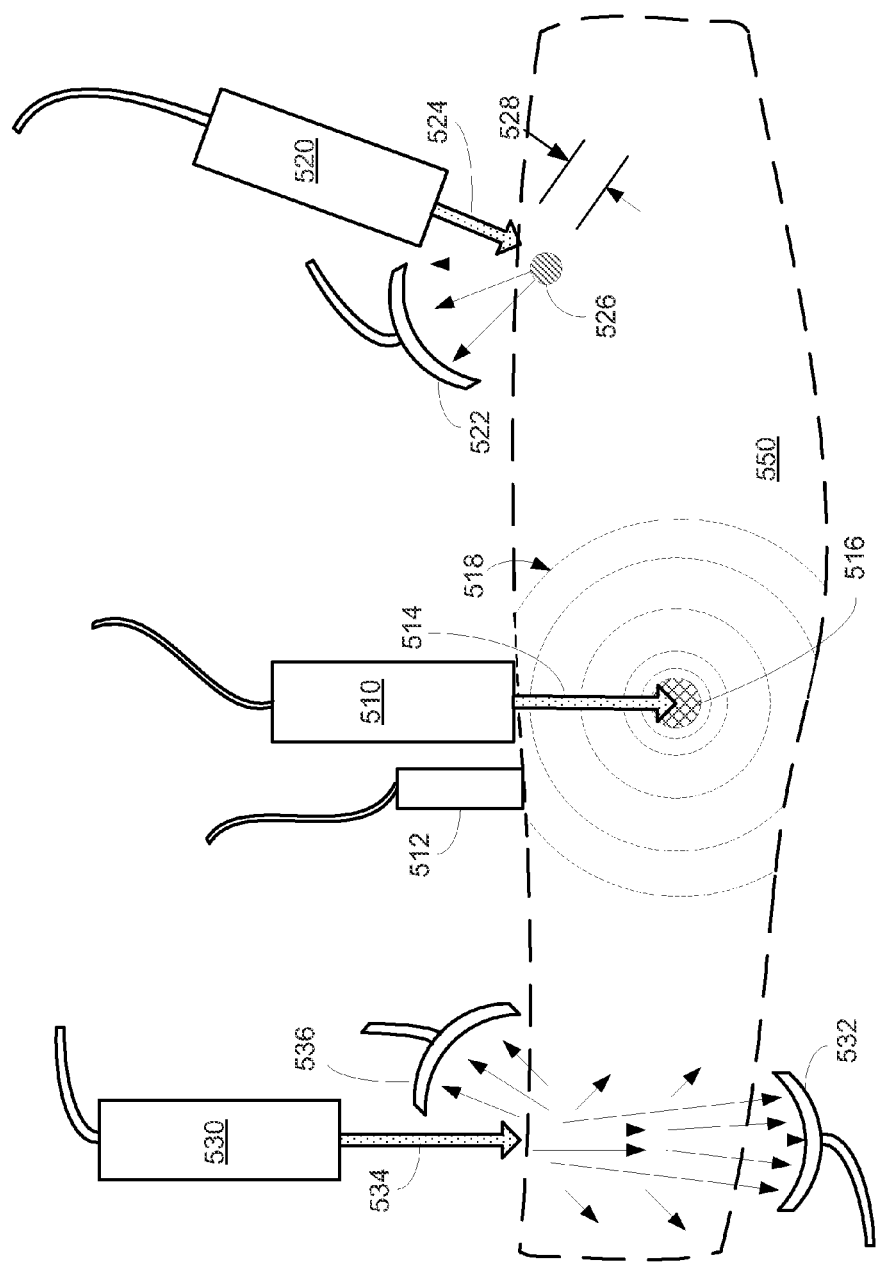
FIG. 5 shows several illustrative photonic and photoacoustic arrangements, in accordance with some embodiments of the present disclosure.

FIG. 5 shows several illustrative photonic and photoacoustic arrangements, in accordance with some embodiments of the present disclosure. A portion of a subject 550 is depicted for illustration of the exemplary PA, OIR, and PDW techniques. An illustrative photoacoustic system, or portion thereof, is shown by light source 510 and acoustic detector 512. A photonic signal 514 from light source 510 may penetrate, and accordingly be attenuated by, tissue of subject 550. Absorption of photonic signal 514, or a portion thereof, by one or more constituents of subject 550 may cause acoustic pressure activity, as shown by acoustic pressure waves 518, in the tissue via the photoacoustic effect. The optical fluence at region 516 (e.g., which may include blood vessels or other biological components) may differ from the optical fluence at the output of light source 510 due to attenuation of the photonic signal by the subject. Optical characterization techniques such as OIR and PDW may be used to determine the optical fluence at region 516. Typically, optical characterization techniques include providing a known photonic signal from a controlled light source to an attenuating media, and detecting at least some of the attenuated photonic signal. A model or simulation may be used to relate, for example, the provided photonic signal, the detected photonic signal, and any suitable optical properties of the attenuating media. In some embodiments, an optical characterization measurement such as an OIR measurement or PDW measurement may be performed near the region of interest (e.g., near the point of incidence of the photonic signal used to generate the photoacoustic effect of the subject). The following discussion of the OIR and PDW techniques includes potentially wavelength-dependent quantities and analyses, as optical properties may be expected to vary with the characteristic wavelength of the light output by the light source. Accordingly, in some embodiments, the OIR technique, PDW technique, or both, may be performed using the same light source as that used to generate the monitored photoacoustic effect of the subject. In some embodiments, the OIR technique, PDW technique, or both, may be performed using a light source other than that used to generate the monitored photoacoustic effect of the subject, but providing light of the same wavelength as that used to generate the monitored photoacoustic effect of the subject. In some embodiments, the OIR technique, PDW technique, or both, may be performed using a light source other than that used to generate the monitored photoacoustic effect of the subject, providing light of a different wavelength from that used to generate the monitored photoacoustic effect of the subject. In some such embodiments, a spectral correlation, correction or other adjustment may be required to apply results of the OIR technique or PDW technique to the photoacoustic analysis.

The OIR technique may include directing light from a light source, the same or different from the PA light source (e.g., a laser or other suitable light source, or combination thereof), towards the surface of an attenuating medium of interest (e.g., tissue) at an oblique angle. The resulting diffuse reflection of the light from the surface may be measured using one or more photodetectors, such as an array of photodiodes, a charge-coupled device (CCD) camera, any other suitable photodetector, or any combination thereof. For example, referencing FIG. 5, photonic signal 524 of light source 520 may be directed to subject 550, and photodetector 522 may detect attenuated light of photonic signal 524. Light source 520, photodetector 522, and any other suitable components may be included in OIR system 408 of FIG. 4. The measured diffuse reflection may be modeled as a diffuse point source located a particular distance along an optical path from the point of incidence of the light on the surface. For example, referencing FIG. 5, attenuated light detected by photodetector 522 may be modeled as originating from a point source 526, located a distance 528 from the point of incidence 525 of photonic signal 524 on the surface of subject 550. Using a diffusion approximation to the radiation equation of transfer, the particular distance may be correlated to an optical diffusivity. The optical diffusivity may further be correlated to an effective attenuation coefficient, which may include the effects of absorption and scattering of the attenuating medium. In some embodiments, the effective attenuation coefficient may be used to estimate the fluence of the PA light source at a spatial location within the media. For example, the effective attenuation coefficient, optical diffusivity, or both, derived from OIR analysis may be used to calculate the fluence of light source 16 of physiological monitoring system 10 at the region of interest in the tissue of subject 40. In a further example, the effective attenuation coefficient, optical diffusivity, or both, may be inputted into a computation model (e.g., such as a Monte Carlo simulation of the radiation transfer equation), to estimate the optical fluence at the region of interest for PA analysis. Accordingly, the resulting estimated fluence may be used in a suitable expression such as, for example, either of Eqs. 1 and 6, or any other suitable expressions, to extract physiological information. In some embodiments, OIR analysis may provide an effective attenuation coefficient which may be different from a constituent absorption coefficient (e.g., as shown in of Eq. 1).

In an illustrative example of the OIR technique, the mean free path (mfp) of photons within an attenuating media (e.g., one or more tissues of a subject), as shown by Eq. 14:

$$mfp = \frac{1}{\mu_a + \mu'_s} \quad (14)$$

may describe an effective length scale of photon transport in the media. In some embodiments, distance 528 of FIG. 5 may be approximated by the mean free path. An optical diffusion coefficient D may be given by the following:

$$D = D(mfp) \quad (15)$$

as some suitable function of the mean free path. For example, the optical diffusion coefficient D may be expressed as mfp/3 in some circumstances. The measured reflectance ρ (e.g., as measured by photodetector 522 of FIG. 5) may be expressed in terms of the optical diffusion coefficient, an effective attenuation coefficient, any other suitable variables, or any combination thereof, as shown illustratively in Eq. 16:

$$\rho = \rho(D, \mu_{\mathit{eff}}) \quad (16)$$

In some embodiments, D and $\mu_{\mathit{eff}}$ may be determined from the OIR measurement. Additionally, Eq. 16 may be cast in terms of the optical diffusion coefficient using Eq. 15, or some other suitable relationship $D = D(\mu_a, \mu'_s)$ may be defined. An additional expression, as shown below:

$$\mu_{\mathit{eff}} = \mu_{\mathit{eff}}(\mu_a, \mu'_s) \quad (17)$$

may be used along with that for the optical diffusion coefficient to determine the unknown absorption coefficient $\mu_a$ and reduced scattering coefficient $\mu'_s$. For example, the effective attenuation coefficient may be expressed as $\mu_{\mathit{eff}} = \sqrt{3\mu_a(\mu_a + \mu'_s)}$. Any suitable mathematical relationships may be used in accordance with the present disclosure.

The PDW technique may include directing light from a modulated light source through an attenuating media of interest. The resulting attenuated light from the media may be measured using one or more photodetectors, such as an array of photodiodes, a charge-coupled device (CCD) camera, any other suitable photodetector, or any combination thereof. For example, referencing FIG. 5, photonic signal 534 of light source 530 may be directed to subject 550. Photodetector 532, photodetector 536, or both, may detect attenuated light (e.g., transmitted and reflected light, respectively) of photonic signal 534. Light source 530, photodetector 532, photodetector 536, any other suitable components, or any combination thereof may be included in PDW system 406 of FIG. 4. PDW system 406 may include one or more photodetectors. In some embodiments, an intensity modulator may be included in PDW system 406, to modulate the photonic signal provided by the light source. The measured attenuated light intensity may be modeled using the radiation transfer equation, with any suitable approximations or simplifications, to determine one or more optical properties such as, for example, an absorption coefficient, a scattering coefficient, or both, or combination thereof. In some embodiments, the determined optical properties may be used to estimate the fluence of the PA light source at a spatial location within the media. For example, the one or more optical properties derived from PDW analysis may be used to calculate the fluence of light source 16 of physiological monitoring system 10 at the region of interest in the tissue of subject 40, using a correlation or other suitable expression. In a further example, the one or more optical properties may be inputted into a computation model (e.g., such as a Monte Carlo simulation of the radiation transfer equation), to estimate the optical fluence at the region of interest for PA analysis. Accordingly, the resulting estimated fluence may be used in a suitable expression such as, for example, Eq. 1, Eq. 6, or any other suitable expression, to extract physiological information.

In some embodiments, processing equipment of system 400 may process a detected PDW signal to determine an amplitude, phase delay, any other suitable properties, or any combination thereof. The amplitude and phase delay of the detected PDW signal, relative to the provided photonic signal, may allow calculation of one or more optical properties of the subject. The phase delay of a detected PDW signal is sensitive to changes in scattering properties of the subject, and the amplitude of a detected PDW signal is sensitive to absorptive properties of the subject (e.g., the concentration of an absorber).

Referencing an illustrative reflective PDW measurement, a photodetector is used to detect reflected light of a photonic signal provided to a subject. Shown in the following Eq. 18:

$$\ln(\rho r) = -r\sqrt{\frac{\mu_a}{D}} + \rho_{DC}(D, K_{DC}) \quad (18)$$

is an expression for the reflectance ρ in terms of the distance between light source and photodetector r, absorption coefficient $\mu_a$, optical diffusion coefficient D, and baseline offset $\rho_{DC}$ cast in terms of the optical diffusion coefficient and the baseline of the source $K_{DC}$. The phase shift Φ is given by the following Eq. 19:

$$\Phi = r\sqrt{\frac{\mu_a}{2D}} \left\{ \left(1 + \left(\frac{\omega}{v\mu_a}\right)^2\right)^{1/2} - 1 \right\}^{1/2} + \Phi'_{DC}(K_\Phi) \quad (19)$$

where ω is the modulation frequency of the light source, v is the speed of light in the subject, and $\Phi'_{DC}$ is the baseline offset of phase cast in terms of relative phase shift of the light source $K_\Phi$. In some embodiments, a two-location PDW detection may be performed. Shown in the following Eq. 20:

$$\Delta \rho_A = -(r_2 - r_1)\sqrt{\frac{\mu_a}{D}} \quad (20)$$

is an expression of the difference in reflectance at two detection locations $r_2$ and $r_1$, which allows the baseline term $\rho_{DC}$ to be discarded. Accordingly, shown in the following Eq. 21:

$$\Delta\Phi = \Phi_2 - \Phi_1 = (r_2 - r_1)\sqrt{\frac{\mu_a}{2D}} \left\{ \left(1 + \left(\frac{\omega}{v\mu_a}\right)^2\right)^{1/2} - 1 \right\}^{1/2} \quad (21)$$

is an expression of the difference in phase shift at the two detection locations $r_2$ and $r_1$, which allows the baseline offset term $\Phi'_{DC}$ to be discarded. Taking the ratio of Eq. 21 to Eq. 20 gives the following Eq. 22:

$$\frac{\Delta\Phi}{\Delta\rho_A} = -\left(\frac{1}{2}\right)^{1/2} \left\{ \left(1 + \left(\frac{\omega}{v\mu_a}\right)^2\right)^{1/2} - 1 \right\}^{1/2} \quad (22)$$

which may be solved for the absorption coefficient, as shown by the following Eq. 23:

$$\mu_a = \frac{\omega}{v} \frac{1}{\left\{ \left(2\left(\frac{\Delta\Phi}{\Delta\rho_A}\right)^2 + 1\right)^2 - 1 \right\}^{1/2}}. \quad (23)$$

Using the following relation for optical diffusion coefficient, $D=1/(3\mu_a+\mu'_s)$, Eq. 20 may be solved for the reduced scattering coefficient, as shown by the following Eq. 24:

$$\mu'_s = \frac{(\Delta\rho_A)^2}{3\mu_a(r_2 - r_1)^2} - \mu_a. \quad (24)$$

The absorption coefficient and reduced scattering coefficient of illustrative Eqs. 23 and 24 may be used to perform further optical analysis. Note that an alternative expression to Eq. 18, may be given by the following Eq. 25:

$$V_d = ZA\frac{S}{4\pi vD}e^{-r\sqrt{\frac{\mu_a}{D}}} \quad (25)$$

for the detector output $V_d$, where Z is the detector responsivity, A is the detection area, and S is the strength of the light source.

Optical properties such as a scattering coefficient, absorption coefficient, and any other suitable properties, determined using OIR, PDW or any other suitable analysis, may be used to determine an optical fluence in a subject. In an illustrative example, which may apply to any suitable optical characterization technique, an expression for the radiative transfer equation in an attenuating medium is shown by Eq. 26:

$$\frac{1}{c}\frac{\delta I(r,\Omega,t)}{\delta t} + \nabla \cdot I(r,\Omega,t)\Omega + \mu_t I(r,\Omega,t) = \quad (26)$$
$$\mu_s \int I(r,\Omega',t)f(\Omega,\Omega')d\Omega' + S(r,\Omega,t),$$

where I(r,Ω,t) is the radiance at position r, solid angle Ω, and time t, c is the speed of light in the medium, $\mu_t$ is the attenuation coefficient, $\mu_s$ is the scattering coefficient, f(Ω,Ω') is the phase function, and S(r,Ω,t) is the radiance source term. An expression for the optical fluence φ(r,t) at location r and time t is shown in Eq. 27:

$$\phi(r,t)=\int I(r,\Omega,t)d\Omega. \quad (27)$$

The radiative transfer equation describes the transport of photons through an attenuating media, and includes the effects of absorption and scattering. Shown in Eq. 28:

$$-D\nabla^2 \phi(r,t) + c\mu_a\phi(r,t) + \frac{\delta\phi(r,t)}{\delta t} = cS_0(r,t) \quad (28)$$

is an illustrative example of a diffusion approximation to the radiative transfer equation, integrated over all solid angles, in which D is the optical diffusion coefficient, and $S_0(r,t)$ is the monopole source term.

It will be understood that the radiative transfer equation, and suitable approximations derived thereof, any other suitable radiative expressions, or any combinations thereof, may be used to model photon attenuation and transport in a subject, in accordance with some embodiments of the present disclosure. For example, an expression such as Eq. 28 may be solved in time, space, or both, to determine the optical fluence at a region of interest of a subject. In a further example, a Fourier transform may be applied to Eq. 28 and the optical fluence may be solved for in the frequency domain. Any suitable computational approach may be used to determine an optical fluence at a region of interest of the subject. In some embodiments, the OIR, PDW, any other suitable technique, or any combination thereof, may be used to determine one or more optical parameters which may be used in an expression such as, for example, Eq. 28.

The foregoing optical characterization techniques are illustrative, and accordingly, any suitable optical characterization techniques, or combination of techniques thereof, may be used in determining an optical fluence at a region of interest.

Figure 6:
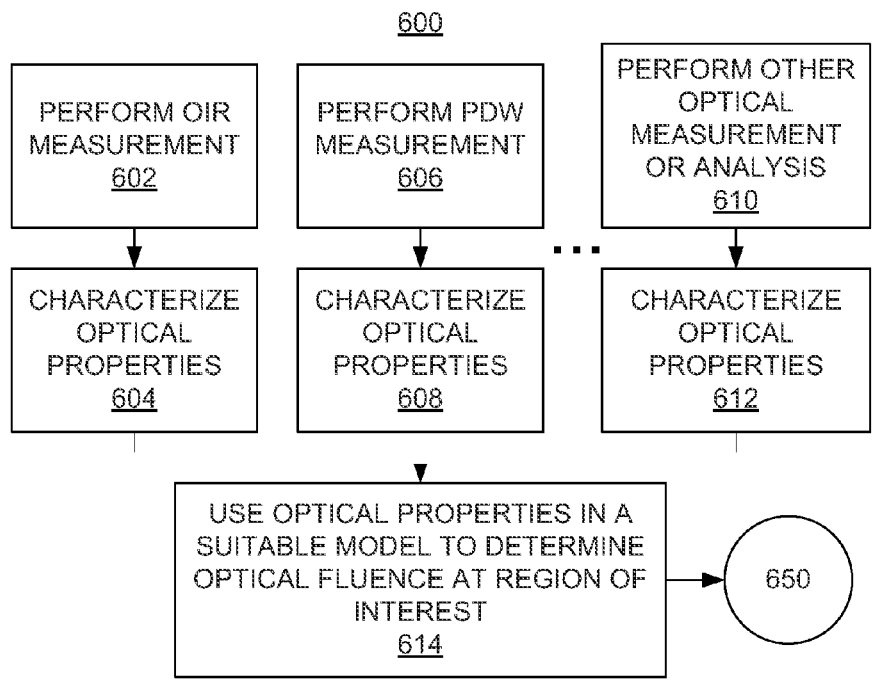
FIG. 6 is a flow diagram of illustrative steps for determining optical fluence at a region of interest, in accordance with some embodiments of the present disclosure.

FIG. 6 is a flow diagram 600 of illustrative steps for determining optical fluence at a region of interest, in accordance with some embodiments of the present disclosure.

Step 602 may include physiological monitoring system 400 performing an OIR measurement on a subject. Step 602 may include a light source of system 400 providing a photonic signal to the subject, or region of the subject thereof, at a particular oblique incident angle. A photodetector of system 400 may detect diffuse reflectance caused by attenuation of the photonic signal.

Step 604 may include processing equipment of physiological monitoring system 400 characterizing one or more optical properties based on the OIR measurement of step 602. In some embodiments, step 604 may include processing equipment of physiological monitoring system 400 inputting a measurement of step 602 into a mathematical expression to calculate the one or more optical properties. In some embodiments, step 604 may include processing equipment of physiological monitoring system 400 using a measurement of step 602 in a lookup table or database to determine the one or more optical properties. The one or more optical properties may include an absorption coefficient, a scattering coefficient, an effective attenuation coefficient, an optical diffusion coefficient, a mean free path, any other suitable optical property, or any combination thereof.

Step 606 may include physiological monitoring system 400 performing a PDW measurement on a subject. Step 602 may include a light source of system 400 providing a photonic signal to the subject, or region of the subject thereof. A photodetector of system 400 may detect attenuated light caused by attenuation of the photonic signal by the subject.

Step 608 may include processing equipment of physiological monitoring system 400 characterizing one or more optical properties based on the PDW measurement of step 606. In some embodiments, step 608 may include processing equipment of physiological monitoring system 400 inputting a measurement of step 606 into a mathematical expression to calculate the one or more optical properties. In some embodiments, step 608 may include processing equipment of physiological monitoring system 400 using a measurement of step 606 in a lookup table or database to determine the one or more optical properties. The one or more optical properties may include an absorption coefficient, a scattering coefficient, an effective attenuation coefficient, an optical diffusion coefficient, a mean free path, any other suitable optical property, or any combination thereof.

Step 610 may include physiological monitoring system 400 performing any other suitable optical measurement on a subject, other than an OIR or PDW measurement. Step 610 may include a light source of system 400 providing a photonic signal to the subject, or region of the subject thereof. A photodetector of system 400 may detect attenuated light caused by attenuation of the photonic signal by the subject.

In some embodiments, step 610 need not include performing a measurement, and may include accessing empirical information (e.g., historical measurement, historical data, sample population data), a mathematical model, and other suitable information, or any combination thereof. For example, step 610 may include processor 312 recalling one or more optical properties or other optical information (e.g., properties affecting optical attenuation) for the subject, which may be stored in any suitable memory (e.g., ROM 52 and/or encoder 42 of system 10). In a further example, step 610 may include processor 312 using a mathematical model to characterize one or more optical parameters based on suitable recalled optical information. In some embodiments, step 610 may include receiving optical information from operator input. For example, an operator may input one or more values or descriptors to system 300, and processor 312 may then characterize optical properties of the subject. In an illustrative example, an operator may input the subject's age and skin color into system 300, and processor 312 may determine effective optical properties based on these descriptors.

Step 612 may include processing equipment of physiological monitoring system 400 characterizing one or more optical properties based on the optical measurement of step 612. In some embodiments, step 612 may include processing equipment of physiological monitoring system 400 inputting a measurement of step 610 into a mathematical expression to calculate the one or more optical properties. In some embodiments, step 612 may include processing equipment of physiological monitoring system 400 using a measurement of step 610 in a lookup table or database to determine the one or more optical properties. The one or more optical properties may include an absorption coefficient, a scattering coefficient, an effective attenuation coefficient, an optical diffusion coefficient, a mean free path, any other suitable optical property, or any combination thereof.

In some embodiments, a single optical characterization may be performed such as, for example, one of steps 602 and 604, steps 606 and 608, or steps 610 and 612. For example, if OIR is used for optical characterization, then PDW or other optical characterization techniques need not be used. In some embodiments, more than one optical characterization technique may be used. For example, both OIR and PDW may be used to determine one or more optical properties of a subject.

Step 614 may include physiological monitoring system 400 using the one or more optical properties in a suitable model to determine the optical fluence at a region of interest (i.e., a spatial location of any suitable size in an attenuating media). In some embodiments, the model may be a mathematical expression. The expression may be a function derived by curve-fitting sample data, an analytic solution to a governing equation, an approximation of a governing equation, any other suitable expression, or any combination thereof. The one or more optical properties may be inputted into the expression, along with any suitable geometric variables describing the region of interest (e.g., a distance), and the optical fluence may be calculated. For example, the expression shown by Eq. 3 provides the optical fluence at a particular spatial location with an effective attenuation coefficient and a distance as inputs. In some embodiments, the model of step 614 may be a computational model. Processing equipment of physiological monitoring system 400 may numerically solve a governing equation to determine the optical fluence at a particular spatial location. For example, a suitable formulation of a radiative transfer equation may be solved numerically using a Monte Carlo technique to determine the optical fluence as a scalar field, or a value at a particular location. In a further example, a suitable formulation of a radiative transfer equation may be solved numerically using a Monte Carlo technique to determine vector field of spectral intensity, with directional resolution, within the media. In some embodiments, the model of step 614 may be a suitable lookup reference table or database. For example, a table of optical fluence values may be indexed by one or more optical properties, geometric variables (e.g., depth of region of interest), light source wavelength, subject information (e.g., skin color, age, sex, bodyfat percentage, vasculature, musculature, or factors that may affect optical properties of a subject). Any suitable technique may be used to determine an optical fluence at a region of interest based at least in part on the one or more optical properties derived from an optical measurement.

Figure 7:
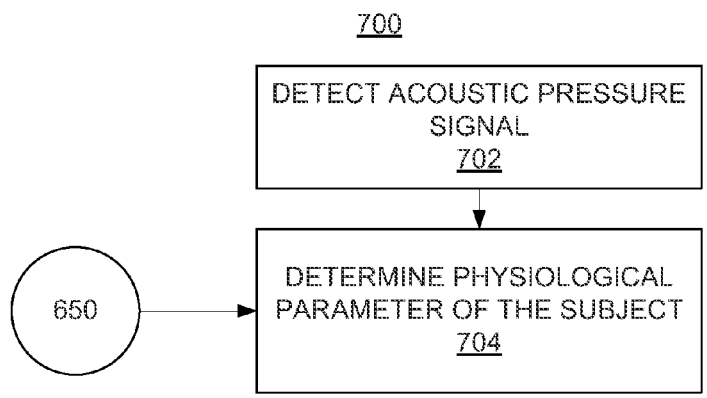
FIG. 7 is a flow diagram of illustrative steps for using an optical characterization and a photoacoustic analysis to determine a physiological parameter of a subject, in accordance with some embodiments of the present disclosure.

FIG. 7 is a flow diagram 700 of illustrative steps for using an optical characterization and a photoacoustic analysis to determine a physiological parameter of a subject, in accordance with some embodiments of the present disclosure.

Step 702 may include physiological monitoring system 400 detecting an acoustic pressure signal. In some embodiments, an acoustic detector such as, for example, an ultrasound detector of physiological monitoring system 400 may detect the acoustic pressure signal. The acoustic detector may output a photoacoustic signal to suitable processing equipment of physiological monitoring system 400. For example, the acoustic detector may output an electrical photoacoustic signal, which may be received by pre-processor 320.

Step 704 may include processing equipment of physiological monitoring system 400 determining one or more physiological parameters of the subject based at least in part on the detected acoustic pressure signal of step 702. Processor 312 may be configured to use a mathematical expression, mathematical model, lookup table, any other suitable reference information, or any combination thereof, to determine the one or more physiological parameters using the photoacoustic signal as an input. In some embodiments, step 704 may include using a determined optical fluence at a region of interest of the subject. For example, any suitable steps of flow diagram 600, as shown by marker 650, may be used to determine the optical fluence at a region of interest of the subject. In some embodiments, the determined optical fluence may aid in determining an absorption coefficient of the subject, from which one or more physiological parameters may be determined.

In some embodiments, the light source used to perform the optical measurement of flow diagram 600 may be the same light source used to provide the photoacoustic response of flow diagram 700. Accordingly, the photonic detector and the acoustic detector may, in some embodiments, be triggered by activation of the light source. For example, in some embodiments, the photonic detector and the acoustic detector may perform detections simultaneously. In a further example, the photonic detector and the acoustic detector may perform respective detections at independent times (e.g., a photonic detection may be performed before or after an acoustic detection). In some embodiments, different light sources may be used to perform the optical measurement and provide the photoacoustic response. In some such embodiments, activation of the light sources may be simultaneous, staggered, or otherwise controlled. For example, TPU 58 of system 10 may be used to control the on-off timing of the light sources (e.g., time division multiplexing). In a further example, TPU 58 of system 10 may be used to control the modulation frequency of each of the light sources (e.g., frequency division multiplexing).

Figure 8:
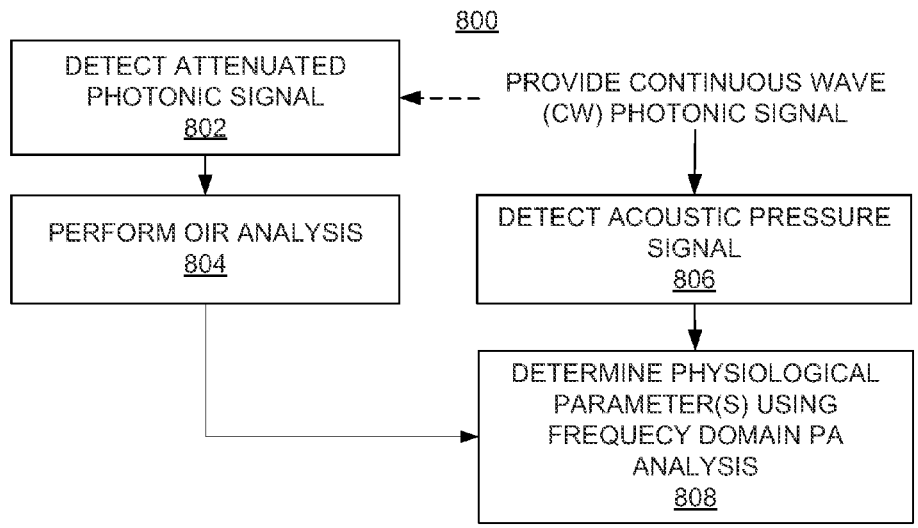
FIG. 8 is a flow diagram of illustrative steps for using an oblique-incidence diffuse reflectance analysis and a photoacoustic analysis to determine a physiological parameter of a subject, in accordance with some embodiments of the present disclosure.

FIG. 8 is a flow diagram 800 of illustrative steps for using an oblique-incidence diffuse reflectance analysis and a photoacoustic analysis to determine a physiological parameter of a subject, in accordance with some embodiments of the present disclosure.

Step 802 may include physiological monitoring system 400 detecting an attenuated photonic signal. One or more suitable photodetectors of physiological monitoring system 400 may be used to detect the attenuated photonic signal. In some embodiments, physiological monitoring system 400 may include a suitable light source configured to provide the photonic signal that undergoes attenuation.

Step 804 may include processing equipment of physiological monitoring system 400 performing OIR analysis on the detected signal photonic signal of step 802, or a signal derived thereof. In some embodiments, step 804 may include processing equipment of physiological monitoring system 400 inputting a measured value of the detected attenuated photonic signal of step 802 into a mathematical expression to calculate the one or more optical properties. In some embodiments, step 804 may include processing equipment of system 400 using a measured value of the detected attenuated photonic signal of step 802 in a lookup table or database to determine the one or more optical properties. The one or more optical properties may include an absorption coefficient, a scattering coefficient, an effective attenuation coefficient, an optical diffusion coefficient, a mean free path, any other suitable optical property, or any combination thereof. In some embodiments, step 804 may include processing equipment of system 400 determining an optical fluence at a region of interest of the subject.

Step 806 may include physiological monitoring system 400 detecting an acoustic pressure signal. In some embodiments, system 400 may include a suitable CW light source configured to provide a CW photonic signal. Absorption of the CW photonic signal, or a portion thereof, by the subject, or a constituent of the subject, may cause an acoustic pressure response in the subject via the photoacoustic effect. In some embodiments, an acoustic detector such as, for example, an ultrasound detector of physiological monitoring system 400 may receive the acoustic pressure signal. The acoustic detector may output a photoacoustic signal to suitable processing equipment of physiological monitoring system 400. For example, the acoustic detector may output an electrical photoacoustic signal, which may be received by pre-processor 320.

In some embodiments, the same CW light source may be used to provide the CW photonic signals referenced in the discussion of steps 802 and 806. Accordingly, step 802 may include detecting an attenuated photonic signal arising from attenuation of the provided CW photonic signal by the subject, and step 806 may include detecting an acoustic response of the subject to the CW photonic signal. In some embodiments, a CW light source may be used to provide the CW photonic signal, and a second light source may be used to provide the photonic signal attenuated by the subject, as detected at step 802. The second light source may be a pulse light source, a CW light source (e.g., and optionally an intensity modulator), any other suitable light source, or any combination thereof. The second light source may provide light of the same wavelength as the CW light source.

Step 808 may include processing equipment of physiological monitoring system 400 determining one or more physiological parameters of the subject based at least in part on the detected acoustic pressure signal of step 806. The processing equipment may perform FD-PA analysis using the detected acoustic signal of step 806. In some embodiments, step 808 may include using an optical fluence at a region of interest of the subject, as determined at step 804, to determine the physiological parameter. In some embodiments, step 808 may include determining the optical fluence at a region of interest of the subject, based on the OIR analysis of step 804. For example, step 804, step 808, or both may include any suitable steps of flow diagram 600 to determine the optical fluence at a region of interest of the subject. In some embodiments, the determined optical fluence may aid in determining an absorption coefficient of the subject, from which one or more physiological parameters may be determined. Physiological parameters determined at step 808 may include pulse rate, blood oxygen saturation (e.g., arterial, venous, or both), hemoglobin concentration (e.g., oxygenated, deoxygenated, or total), any other suitable physiological parameters, or any combination thereof. In some embodiments, step 808 may include using the correlation technique (e.g., as described herein in the context of Eqs. 8-11), the heterodyne mixing technique (e.g., as described herein in the context of Eqs.

12-13), any other suitable technique, or any combination thereof to perform the FD-PA analysis.

Figure 9:
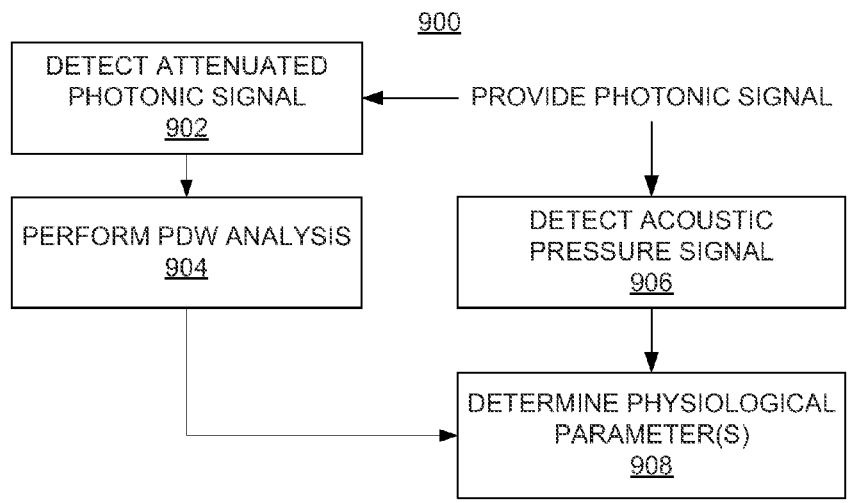
FIG. 9 is a flow diagram of illustrative steps for using a photon density wave analysis and a photoacoustic analysis to determine a physiological parameter of a subject, in accordance with some embodiments of the present disclosure.

FIG. 9 is a flow diagram 900 of illustrative steps for using a photon density wave analysis and a photoacoustic analysis to determine a physiological parameter of a subject, in accordance with some embodiments of the present disclosure.

Step 902 may include physiological monitoring system 400 detecting an attenuated photonic signal. One or more suitable photodetectors of physiological monitoring system 400 may be used to detect the attenuated photonic signal. In some embodiments, physiological monitoring system 400 may include a suitable light source configured to provide the photonic signal that undergoes attenuation.

Step 904 may include processing equipment of physiological monitoring system 400 performing PDW analysis on the detected signal photonic signal of step 902, or a signal derived thereof. In some embodiments, step 904 may include processing equipment of physiological monitoring system 400 inputting a measured value of the detected attenuated photonic signal of step 902 into a mathematical expression to calculate the one or more optical properties. In some embodiments, step 904 may include processing equipment of system 400 using a measured value of the detected attenuated photonic signal of step 902 in a lookup table or database to determine the one or more optical properties. The one or more optical properties may include an absorption coefficient, a scattering coefficient, an effective attenuation coefficient, an optical diffusion coefficient, a mean free path, any other suitable optical property, or any combination thereof. In some embodiments, step 904 may include processing equipment of system 400 determining an optical fluence at a region of interest of the subject.

Step 906 may include physiological monitoring system 400 detecting an acoustic pressure signal. In some embodiments, system 400 may include a suitable light source (pulsed or CW) configured to provide a photonic signal. Absorption of the photonic signal, or a portion thereof, by the subject, or a constituent of the subject, may cause an acoustic pressure response in the subject via the photoacoustic effect. In some embodiments, an acoustic detector such as, for example, an ultrasound detector of physiological monitoring system 400 may receive the acoustic pressure signal. The acoustic detector may output a photoacoustic signal to suitable processing equipment of physiological monitoring system 400. For example, the acoustic detector may output an electrical photoacoustic signal, which may be received by pre-processor 320.

In some embodiments, the same light source may be used to provide the photonic signals referenced in the discussion of steps 902 and 906. Accordingly, step 902 may include detecting an attenuated photonic signal arising from attenuation of the provided photonic signal by the subject, and step 906 may include detecting an acoustic response of the subject to the photonic signal. In some embodiments, a first light source may be used to provide the photonic signal attenuated by the subject, as detected at step 902, and a second light source may be used to provide the photonic signal that causes the photoacoustic response as detected at step 906. Either of the first and second light sources may be a pulsed light source, a CW light source (e.g., and optionally an intensity modulator), any other suitable light source, or any combination thereof. The second light source may provide light of the same wavelength as the first light source.

Step 908 may include processing equipment of physiological monitoring system 400 determining one or more physiological parameters of the subject based at least in part on the detected acoustic pressure signal of step 906. In some embodiments, step 908 may include using an optical fluence at a region of interest of the subject, as determined at step 904, to determine the physiological parameter. In some embodiments, step 908 may include determining the optical fluence at a region of interest of the subject, based on the PDW analysis of step 904. For example, step 904, step 908, or both may include any suitable steps of flow diagram 600 to determine the optical fluence at a region of interest of the subject. In some embodiments, the determined optical fluence may aid in determining an absorption coefficient of the subject, from which one or more physiological parameters may be determined. Physiological parameters determined at step 808 may include pulse rate, blood oxygen saturation (e.g., arterial, venous, or both), hemoglobin concentration (e.g., oxygenated, deoxygenated, or total), any other suitable physiological parameters, or any combination thereof.

Referring to Eq. 1, the fluence $\phi(z)$ may be estimated using the illustrative techniques described herein (e.g., the OIR and/or PDW techniques), and the Grüneisen parameter may be known. By rearranging Eq. 1, the following equation can be obtained:

$$\mu_a = \frac{p(z)}{\Gamma \phi(z)} \quad (29)$$

for the absorption coefficient $\mu_a$ of the absorbing tissue (hemoglobin of the subject's blood in this example). In some embodiments, the wavelength of the light source may be selected to aid in determining one or more physiological parameters. For example, at a first wavelength $\lambda_1$ where oxy-hemoglobin and deoxy-hemoglobin have approximately the same absorptivity (e.g., around 808 nm), the absorption coefficient $\mu_{a,\lambda_1}$ may be given by the following:

$$\mu_{a,\lambda_1} = tHb \cdot \epsilon_{\lambda_1}, \quad (30)$$

where $\epsilon_{\lambda_1}$ (presumed known) is the absorptivity of the oxy-hemoglobin and deoxy-hemoglobin at first wavelength $\lambda_1$. Eq. 30 may be solved for tHb from the known $\mu_{a,\lambda_1}$ (e.g., known from using Eq. 29). In some embodiments, a second light source of a second wavelength $\lambda_2$, different from the first, may be used to determine blood oxygen saturation. For example, with tHb known, a second absorption coefficient may be determined at the second wavelength. The absorption coefficient $\mu_a$ may be given by the following:

$$\mu_{a,\lambda_2} = \epsilon_{ox,\lambda_2} c_{ox} + \epsilon_{deox,\lambda_2} c_{deox}, \quad (31)$$

where $\epsilon_{ox,\lambda_2}$ is the absorptivity of oxy-hemoglobin, $\epsilon_{deox,\lambda_2}$ is the absorptivity of deoxy-hemoglobin, $c_{ox}$ is the concentration of oxy-hemoglobin, and $c_{deox}$ is the concentration of deoxy-hemoglobin. The concentration can be related by:

$$tHb = c_{ox} + c_{deox}, \quad (32)$$

which may be combined with Eq. 31 to give:

$$\mu_{a,\lambda_2} = \epsilon_{ox,\lambda_2} c_{ox} + \epsilon_{deox,\lambda_2}(tHb - c_{ox}), \text{ or} \quad (33)$$

$$\mu_{a,\lambda_2} = \epsilon_{ox,\lambda_2}(tHb - c_{deox}) + \epsilon_{deox,\lambda_2} c_{deox}. \quad (34)$$

Because tHb is known, any of Eqs. 33 and 34 may be inverted to determine the respective hemoglobin concentration from the known tHb and $\mu_{a,\lambda_2}$. Additionally, blood oxygen saturation $S_{O2}$ may be determined by the following:

$$S_{O2} = \frac{c_{ox}}{c_{ox} + c_{deox}}, \quad (35)$$

which may be an arterial blood oxygen saturation or venous oxygen saturation depending upon the type of blood vessel. It will be understood that Eqs. 30-35 provide illustrative examples of formulas used to determine physiological parameters from photoacoustic measurements. Any suitable equations, models, other suitable mathematical construct, look-up table, database, or other reference may be used to determine one or more physiological parameters based on two photoacoustic peaks. For example, in some embodiments, physiological parameters may be tabulated (e.g., in a look-up table stored in encoder 42 of system 10) for discrete values of absorption coefficient at one or more wavelengths. In some embodiments, a pulse rate may be determined based on modulations of detected signals, or parameters derived thereof, at the frequency of the pulse rate. For example, an artery may be monitored, and the pumping of the subject's heart may cause a modulation of detected signals at the frequency of the heart rate.

Figure 10:
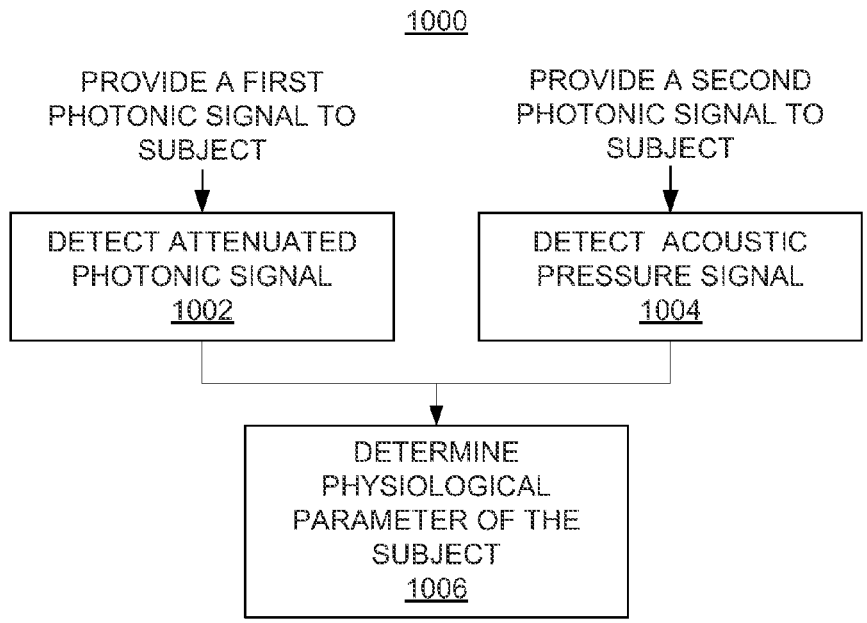
FIG. 10 is a flow diagram of illustrative steps for using a detected attenuated photonic signal and a photoacoustic analysis to determine a physiological parameter of a subject, in accordance with some embodiments of the present disclosure.

FIG. 10 is a flow diagram 1000 of illustrative steps for using a detected attenuated photonic signal and a photoacoustic analysis to determine a physiological parameter of a subject, in accordance with some embodiments of the present disclosure.

Step 1002 may include physiological monitoring system 400 detecting an attenuated photonic signal. One or more suitable photodetectors of physiological monitoring system 400 may be used to detect the attenuated photonic signal. In some embodiments, physiological monitoring system 400 may include a suitable first light source configured to provide the photonic signal that undergoes attenuation.

Step 1004 may include physiological monitoring system 400 detecting an acoustic pressure signal. In some embodiments, system 400 may include a suitable second light source (pulsed or CW) configured to provide a second photonic signal. Absorption of the second photonic signal, or a portion thereof, by the subject, or a constituent of the subject, may cause an acoustic pressure response in the subject via the photoacoustic effect. In some embodiments, an acoustic detector such as, for example, an ultrasound detector of physiological monitoring system 400 may receive the acoustic pressure signal. The acoustic detector may output an electrical signal to suitable processing equipment of physiological monitoring system 400.

Step 1006 may include processing equipment of physiological monitoring system 400 determining one or more physiological parameters of the subject based at least in part on the detected attenuated photonic signal of step 1002, and based at least in part on the acoustic pressure signal of step 1004. In some embodiments, step 1006 may include determining the optical fluence at a region of interest of the subject, based on the detected attenuated photonic signal of step 1002. For example, step 1006 may include any suitable steps of flow diagrams 600, 800 and 900 (e.g., OIR analysis, PDW analysis) to determine the optical fluence at a region of interest of the subject. In some embodiments, the determined optical fluence may aid in determining an absorption coefficient of the subject, from which one or more physiological parameters may be determined. Physiological parameters determined at step 1006 may include pulse rate, blood oxygen saturation (e.g., arterial, venous, or both), hemoglobin concentration (e.g., oxygenated, deoxygenated, or total), any other suitable physiological parameters, or any combination thereof.

In some embodiments, an optical measurement may include a photoplethysmographic (PPG) measurement of the subject, which may be used with a photoacoustic measurement to determine one or more physiological parameters. A PPG measurement may be taken using any suitable oximeter such as, for example, a two wavelength pulse oximeter. For example, the first photonic signal of flow diagram 1000 may include light of two wavelengths. In some such examples, step 1006 may include determining a blood oxygen saturation based on the detected attenuated photonic signal. In some embodiments, a $SpO_2$ measurement may be used as an adjustment factor to determine total hemoglobin concentration, or other suitable physiological parameter, which may be further used to determine a venous oxygen saturation. The $SpO_2$ measurement may be provided by any suitable pulse oximeter system, which may be separate from physiological monitoring system 10, integrated in physiological monitoring system 10 (e.g., a pulse oximeter module included in physiological monitoring system 400), communicatively coupled to physiological monitoring system 10, in any other suitable configuration, or any combination thereof. In some circumstances, such as a subject experiencing hypoxia, the use of a PPG measurement may be especially useful in adjusting a total hemoglobin value.

An oximeter may include a light sensor that is placed at a site on a subject, typically a fingertip, toe, forehead or earlobe, or in the case of a neonate, across a foot. The oximeter may use a light source (e.g., one or more light emitting diodes) to pass light through blood perfused tissue and photoelectrically sense the absorption of the light in the tissue. For example, additional suitable sensor locations include, without limitation, the neck to monitor carotid artery pulsatile flow, the wrist to monitor radial artery pulsatile flow, the inside of a subject's thigh to monitor femoral artery pulsatile flow, the ankle to monitor tibial artery pulsatile flow, and around or in front of the ear. Suitable sensors for these locations may include sensors for sensing absorbed light based on detecting reflected light. In all suitable locations, for example, the oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxy-hemoglobin) being measured as well as a pulse rate and when each individual pulse occurs.

In some applications, the light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared (IR) wavelengths may be used because that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood.

Figure 11:
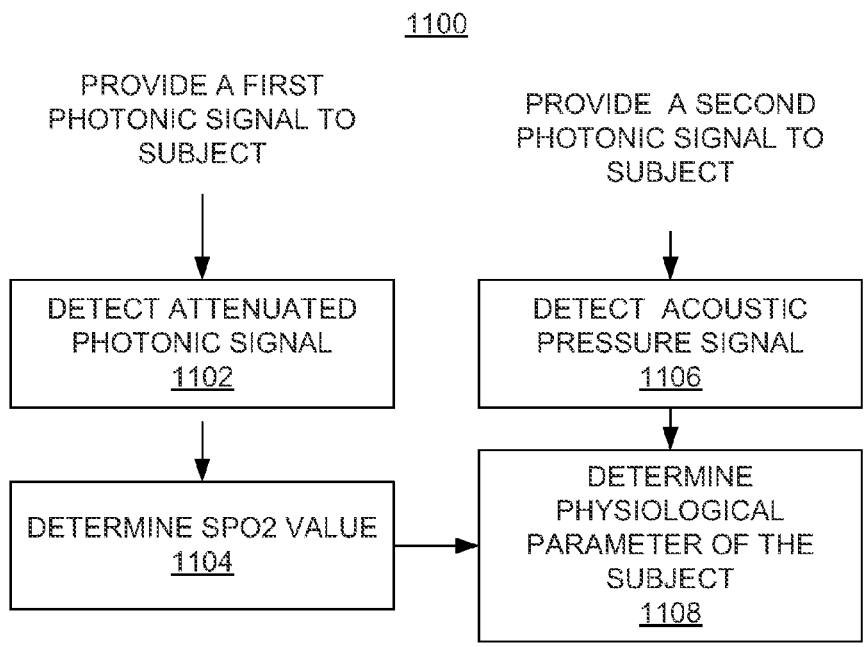
FIG. 11 is a flow diagram of illustrative steps for using a measured SpO2 value and a photoacoustic analysis to determine a physiological parameter of a subject, in accordance with some embodiments of the present disclosure.

FIG. 11 is a flow diagram 1100 of illustrative steps for using a measured $SpO_2$ value and a photoacoustic analysis to determine a physiological parameter of a subject, in accordance with some embodiments of the present disclosure.

Step 1102 may include physiological monitoring system 400 detecting an attenuated photonic signal. One or more suitable photodetectors of physiological monitoring system 400 may be used to detect the attenuated photonic signal. In some embodiments, the one or more photodetectors may be triggered by light drive circuitry to detect multiplexed photonic signals. For example, a time division multiplexed (TDM) photonic signal of RED, IR, and ambient light may be detected by the one or more photodetectors, and de-multiplexed by processing equipment of system 400. In some embodiments, a suitable light source of system 400 may provide the first photonic signal to the subject. In some embodiments, the light source may include LEDs of two wavelengths (e.g., one RED and one IR). For example, system 400 may include oximeter system 404, which may include both LEDs and a suitable light drive circuit. The LEDs may be driven using any suitable technique such as, for example, TDM, frequency division multiplexing (FDM), code-division multiplexing (CDM), any other suitable multiplexing technique, any suitable modulating technique, or any combination thereof.

Step 1104 may include suitable processing equipment of system 400 determining an SpO2 value based at least in part on the detected attenuated photonic signal of step 1102. A convenient starting point for determining the oxygen saturation of hemoglobin assumes a saturation calculation based at least in part on Lambert-Beer's law. The following notation will be used herein:

$$I(\lambda,t) = I_0(\lambda) \exp(-(s\beta_0(\lambda) + (1-s)\beta_r(\lambda))l(t)). \tag{36}$$

where:

$\lambda$ = wavelength;

$t$ = time;

$I$ = intensity of light detected;

$I_0$ = intensity of light transmitted;

$s$ = oxygen saturation;

$\beta_0, \beta_r$ = empirically derived absorption coefficients; and $l(t)$ = a combination of concentration and path length from emitter to detector as a function of time.

In some embodiments, system 400 measures light absorption at two wavelengths (e.g., Red and IR), and then calculates saturation by solving for the "ratio of ratios" as follows.

1. The natural logarithm of Eq. 36 is taken ("log" will be used to represent the natural logarithm) for IR and Red to yield:

$$\log I = \log I_0 - (s\beta_0 + (1-s)\beta_r)l(t)). \tag{37}$$

2. Eq. 37 is then differentiated with respect to time to yield the following:

$$\frac{d\log I}{dt} = -(s\beta_0 + (1-s)\beta_r)\frac{dl}{dt}. \tag{38}$$

3. Eq. 38, evaluated at the Red wavelength $\lambda_R$, is divided by Eq. 38 evaluated at the IR wavelength $\lambda_{IR}$ in accordance with the following:

$$\frac{d\log I(\lambda_R)/dt}{d\log I(\lambda_{IR})/dt} = \frac{-(s\beta_0(\lambda_R) + (1-s)\beta_r(\lambda_R))}{-(s\beta_0(\lambda_{IR}) + (1-s)\beta_r(\lambda_{IR}))}. \tag{39}$$

4. Solving for s yields the following:

$$s = \frac{\frac{d\log I(\lambda_R)}{dt}\beta_r(\lambda_R) - \frac{d\log I(\lambda_R)}{dt}\beta_r(\lambda_{IR})}{\frac{d\log I(\lambda_R)}{dt}(\beta_0(\lambda_{IR}) - \beta_r(\lambda_{IR})) - \frac{d\log I(\lambda_{IR})}{dt}(\beta_0(\lambda_R) - \beta_r(\lambda_R))}. \tag{40}$$

5. Note that, in discrete time, the following approximation can be made:

$$\frac{d\log I(\lambda, t)}{dt} \cong \log I(\lambda, t_2) - \log I(\lambda, t_1). \tag{41}$$

6. Rewriting Eq. 41 yields the following:

$$\frac{d\log I(\lambda, t)}{dt} \cong \log\left(\frac{I(\lambda, t_2)}{I(\lambda, t_1)}\right). \tag{42}$$

7. Thus, Eq. 39 can be expressed as follows:

$$\frac{\frac{d\log I(\lambda_R)}{dt}}{\frac{d\log I(\lambda_{IR}, t)}{dt}} \cong \frac{\log\left(\frac{I(\lambda_R, t_1)}{I(\lambda_R, t_2)}\right)}{\log\left(\frac{I(\lambda_{IR}, t_1)}{I(\lambda_{IR}, t_2)}\right)} = R, \tag{43}$$

where R represents the "ratio of ratios."

8. Solving Eq. 39 for s using the relationship of Eq. 40 yields:

$$s = \frac{\beta_r(\lambda_R) - R\beta_r(\lambda_{IR})}{R(\beta_0(\lambda_{IR}) - \beta_r(\lambda_{IR})) - \beta_0(\lambda_R) + \beta_r(\lambda_R)}. \tag{44}$$

9. From Eq. 43, R can be calculated using two points (e.g., PPG maximum and minimum), or a family of points. One method applies a family of points to a modified version of Eq. 43. Using the following relationship:

$$\frac{d\log I}{dt} = \frac{dI/dt}{I}, \tag{45}$$

Eq. 43 becomes $$\frac{\frac{d\log I(\lambda_R)}{dt}}{\frac{d\log I(\lambda_{IR}, t)}{dt}} \cong \frac{\frac{I(\lambda_R, t_2) - I(\lambda_R, t_1)}{I(\lambda_R, t_1)}}{\frac{I(\lambda_{IR}, t_2) - I(\lambda_{IR}, t_1)}{I(\lambda_{IR}, t_1)}} \tag{46}$$

$$= \frac{(I(\lambda_R, t_2) - I(\lambda_R, t_1))I(\lambda_{IR}, t_1)}{(I(\lambda_{IR}, t_2) - I(\lambda_{IR}, t_1))I(\lambda_R, t_1)}$$

$$= R,$$

which defines a cluster of points whose slope of y versus x will give R when $$x = (I(\lambda_{IR}, t_2) - I(\lambda_{IR}, t_1))(\lambda_R, t_1), \tag{47}$$

and $$y = (I(\lambda_R, t_2) - I(\lambda_R, t_1))I(\lambda_{IR}, t_1). \tag{48}$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

Step 1106 may include physiological monitoring system 400 detecting an acoustic pressure signal. Absorption of a second photonic signal, or a portion thereof, by the subject, or a constituent of the subject, may cause an acoustic pressure response in the subject via the photoacoustic effect. In some embodiments, an acoustic detector such as, for example, an ultrasound detector of physiological monitoring system 400 may receive the acoustic pressure signal. The acoustic detector may output an electrical signal to suitable processing equipment of physiological monitoring system 400. In some embodiments, a suitable light source of system 400 may provide the second photonic signal to the subject. In some embodiments, the second photonic signal may be provided to the subject to cause a photoacoustic response within the subject. The second photonic signal may be pulsed, CW, modulated, any other suitable type of photonic signal, or any combination thereof. For example, in some embodiments, the second photonic signal may be a CW photonic signal, modulated using a linear frequency modulation (e.g., a "chirp" modulation). In a further example, in some embodiments, the second photonic signal may include pulses of nanosecond-scale pulses. In some embodiments, the second photonic signal may be spatially modulated. For example, the second photonic signal may be focused using optics to increase spatial resolution.

Step 1108 may include processing equipment of physiological monitoring system 400 determining one or more physiological parameters of the subject based at least in part on the detected acoustic pressure signal of step 1106 and based at least in part on the determined $SpO_2$ value of step 1104. In some embodiments, step 1108 may include determining (e.g., estimating) the optical fluence at a region of interest of the subject. Physiological parameters determined at step 808 may include pulse rate, blood oxygen saturation (e.g., arterial, venous, or both), hemoglobin concentration (e.g., oxygenated, deoxygenated, or total), any other suitable physiological parameters, or any combination thereof.

In an illustrative example of step 1108 of flow diagram 1100, a photoacoustic system may use a 905 nanometer pulsed laser to supply a photonic signal to each of an artery (the carotid artery in this example) and a vein (the jugular vein in this example), both located in the subject's neck. In some embodiments, the pulsed light source may be relatively cheaper, compact, or both as compared to other light sources. Shown in Eqs. 49 and 50:

$$P_a(z_a) = \Gamma \mu_{a,a} \phi_0 e^{-\mu_{eff} z_a} \quad (49)$$

$$P_v(z_v) = \Gamma \mu_{a,v} \phi_0 e^{-\mu_{eff} z_v} \quad (50)$$

are expressions for received photoacoustic signals $P_a(z_a)$ and $P(z)$ of the carotid artery and jugular vein, respectively. Accordingly, the region of interest is different for the carotid artery relative to the jugular vein, as indicated by artery position $z_a$ and vein position $z_v$. In some embodiments, the initial optical fluence $\phi_0$, and Grüneisen parameter $\Gamma$ of Eqs. 49 and 50 may be combined into coefficient K, as shown by respective Eqs. 51 and 52. It will be understood that, in some embodiments, the optical fluence at the region of interest may be determined using a computational model (e.g., a Monte Carlo simulation), rather than a single mathematical formula as in the present example. Coefficient K may have a constant value for a particular arrangement and region of interest, and accordingly is treated as a constant in this example. In the following Eqs. 51 and 52:

$$P_{a,corr} = K\mu_{a,a} = K(c_{ox,a}\epsilon_{ox,\lambda} + c_{Hb,a}\epsilon_{Hb,\lambda}) \quad (51)$$

$$P_{v,corr} = K\mu_{a,v} = K(c_{ox,v}\epsilon_{ox,\lambda} + c_{Hb,v}\epsilon_{Hb,\lambda}) \quad (52)$$

the effective absorption coefficients have been replaced with expressions which include arterial and venous oxy-hemoglobin concentration ($c_{ox,a}$ and $c_{ox,v}$), arterial and venous deoxy-hemoglobin concentration ($c_{Hb,a}$ and $c_{Hb,v}$), spectral oxy-hemoglobin extinction coefficient $\epsilon_{ox,\lambda}$, and spectral deoxy-hemoglobin extinction coefficient $\epsilon_{Hb,\lambda}$, in which $\lambda$ is the wavelength of the pulsed light source (e.g., 905 nm in this example). Note that the "corrected" photoacoustic signals $P_{a,corr}$ and $P_{v,corr}$ include (e.g., via division) the respective exponential depth correction factors $e^{-\mu_{eff} z_a}$ and $e^{-\mu_{eff} z_v}$. A further mathematical relationship, shown by Eq. 53:

$$SpO_2 = \frac{c_{ox,a}}{c_{ox,a} + c_{Hb,a}} \quad (53)$$

among the arterial oxy-hemoglobin and deoxy-hemoglobin concentrations may be extracted from an $SpO_2$ measurement taken using a pulse oximeter, for example. The $SpO_2$ measurement may be taken at a finger digit, forehead, or other suitable location of the subject. A combination of Eqs. 51 and 53 leads to Eq. 54:

$$c_{ox,a} = \frac{P_{a,corr}}{K\left(\epsilon_{ox,\lambda} + \frac{1-SpO_2}{SpO_2}\epsilon_{Hb,\lambda}\right)} \quad (54)$$

which is an expression for the arterial oxy-hemoglobin concentration. Accordingly, shown by Eq. 55:

$$c_{Hb,a} = \frac{1-SpO_2}{SpO_2} c_{ox,a} \quad (55)$$

a corresponding expression for the arterial deoxy-hemoglobin concentration may also be derived. Note that for a subject with a blood oxygen saturation near unity (i.e., 100%), the arterial deoxy-hemoglobin concentration may be a relatively small number, and accordingly may be ignored in some circumstances. In some such cases, the total hemoglobin concentration is then approximately equal to the arterial oxy-hemoglobin concentration. Eqs. 54 and 55 may be summed, as shown by Eq. 56:

$$t_{HB} = c_{ox,a} + c_{Hb,a} = c_{ox,v} + c_{Hb,v} \quad (56)$$

to determine the total hemoglobin concentration, which is independent of oxygen saturation. A combination of Eqs. 44 and 56 is shown by Eq. 57:

$$c_{ox,v} = \frac{\frac{P_{v,corr}}{K} - t_{HB}\epsilon_{Hb,\lambda}}{\epsilon_{ox,\lambda} - \epsilon_{Hb,\lambda}} \quad (57)$$

from which the venous oxygen saturation may be determined, as shown by Eq. 58:

$$SvO_2 = \frac{c_{ox,v}}{t_{HB}} * 100\% \quad (58)$$

where the venous oxygen saturation $SvO_2$ is given in percentage. Accordingly, step 1112 of flow diagram 1100 may include determining a venous oxygen saturation, any other suitable physiological parameter, or any combination thereof.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed is:

1. A physiological monitoring system for monitoring a subject, the system comprising:
    at least one photodetector configured to detect a first photonic signal attenuated by the subject, wherein the first photonic signal comprises light of two different wavelengths;
    at least one acoustic detector configured to detect an acoustic pressure signal from the subject, wherein the acoustic pressure signal is caused by absorption of a second photonic signal by at least one constituent of the subject; and
    processing equipment communicatively coupled to the at least one acoustic detector and the at least one photodetector, the processing equipment configured to:
        determine an SpO2 value based at least in part on the attenuated first photonic signal;
        determine a first hemoglobin concentration value based at least in part on the determined SpO2 value, and based at least in part on the detected acoustic pressure signal; and
        determine a second hemoglobin concentration value based at least in part on the first hemoglobin concentration value and based at least in part on the determined SpO2 value.

2. The system of claim 1, further comprising a first light source configured to provide the first photonic signal to the subject.

3. The system of claim 2, wherein the first light source comprises:
    a first light emitting diode configured to provide a first wavelength of the two different wavelengths; and
    a second light emitting diode configured to provide a second wavelength of the two different wavelengths.

4. The system of claim 3, wherein the first wavelength comprises a wavelength in the red spectrum, and wherein the second wavelength comprises a wavelength in the infrared spectrum.

5. The system of claim 1, further comprising a second light source configured to provide the second photonic signal to the subject.

6. The system of claim 5, wherein the second light source comprises an intensity modulator, and wherein the second photonic signal comprises a modulated photonic signal.

7. The system of claim 1, wherein the first hemoglobin concentration value comprises an arterial oxy-hemoglobin concentration value.

8. The system of claim 1, wherein the second hemoglobin concentration value comprises a total hemoglobin concentration value.

9. The system of claim 1, wherein the processing equipment is further configured to determine a venous oxygen saturation value based at least in part on the determined SpO2 value.

10. The system of claim 1, wherein the first hemoglobin concentration value comprises an oxy-hemoglobin concentration value and wherein the second hemoglobin concentration value comprises a total hemoglobin concentration value.

11. A method for monitoring a physiological parameter of a subject, the method comprising:
    detecting a first photonic signal attenuated by the subject, wherein the first photonic signal comprises light of two different wavelengths;
    detecting an acoustic pressure signal from the subject, wherein the acoustic pressure signal is caused by absorption of a second photonic signal by at least one constituent of the subject;
    determining an SpO2 value based at least in part on the attenuated first photonic signal;
    determining a first hemoglobin concentration value based at least in part on the determined SpO2 value, and based at least in part on the detected acoustic pressure signal; and
    determining a second hemoglobin concentration value based at least in part on the first hemoglobin concentration value and based at least in part on the determine SpO2 value.

12. The method of claim 11, further comprising providing the first photonic signal to the subject.

13. The method of claim 12, wherein the providing the first photonic signal to the subject further comprises:
    provide the light of the first wavelength of the two different wavelengths using a first light emitting diode; and
    provide the light of the second wavelength of the two different wavelengths using a second light emitting diode.

14. The method of claim 13, wherein the first wavelength comprises a wavelength in the red spectrum, and wherein the second wavelength comprises a wavelength in the infrared spectrum.

15. The method of claim 11, further comprising providing the second photonic signal to the subject.

16. The method of claim 15, further comprising modulating the intensity of the second photonic signal before attenuation of the second photonic signal by the subject.

17. The method of claim 11, wherein the first hemoglobin concentration value comprises an arterial oxy-hemoglobin concentration.

18. The method of claim 11, wherein the second hemoglobin concentration value comprises a total hemoglobin concentration value.

19. The method of claim 11, further comprising determining a venous oxygen saturation value based at least in part on the determined SpO2 value.

20. The method of claim 11, wherein first hemoglobin concentration value comprises an oxy-hemoglobin concentration value and wherein the second hemoglobin concentration value comprises a total hemoglobin concentration value.

* * * * *